US005747485A

United States Patent [19]

Doherty et al.

[11] Patent Number: 5,747,485

[45] Date of Patent: May 5, 1998

[54] SUBSTITUTED AZETIDIONES AS ANTI-INFLAMMATORY AND ANTIDEGENERATIVE AGENTS

[75] Inventors: James Doherty, Montvale; Conrad Dorn, Plainfield; Philippe Durette, New Providence; Paul Finke, Milltown; Malcolm Maccoss, Freehold; Sander Mills, Woodbridge; Shrenik Shah, Metuchen; Soumya Sahoo, Old Bridge; William Hagmann; Jeffrey Hale, both of Westfield; Thomas Lanza, Edison, all of N.J.

[73] Assignee: Merck & Co., Inc., Rahway, N.J.

[21] Appl. No.: 848,076

[22] Filed: Jun. 5, 1997

Related U.S. Application Data

[63] Continuation of Ser. No. 416,771, Apr. 13, 1995, abandoned, filed as PCT/US93/10268, Oct. 26, 1993.

[51] Int. Cl.$^6$ .................... A61K 31/395

[52] U.S. Cl. .................... 514/210

[58] Field of Search .................... 514/210

[56] References Cited

U.S. PATENT DOCUMENTS

| | | | |
|---|---|---|---|
| 4,064,120 | 12/1977 | Krapcho et al. | 544/111 |
| 4,115,382 | 9/1978 | Krapcho et al. | 544/359 |
| 4,166,907 | 9/1979 | Krapcho et al. | 544/111 |
| 4,174,317 | 11/1979 | Krapcho | 544/111 |
| 4,260,743 | 4/1981 | Bose | 546/275 |
| 4,510,086 | 4/1985 | Ross et al. | 540/360 |
| 4,534,896 | 8/1985 | Treuner et al. | 514/210 |
| 4,559,335 | 12/1985 | Zahler | 546/275 |
| 4,576,749 | 3/1986 | Zahler et al. | 544/311 |
| 4,680,391 | 7/1987 | Firestone et al. | 540/200 |
| 5,229,381 | 7/1993 | Doherty et al. | 514/210 |
| 5,348,953 | 9/1994 | Doherty et al. | 514/210 |

FOREIGN PATENT DOCUMENTS

| | | |
|---|---|---|
| 295 547 | 2/1970 | Austria . |
| 375 640 | 9/1981 | Austria . |
| 0 023 097 | 1/1981 | European Pat. Off. . |
| 0 042 026 | 12/1981 | European Pat. Off. . |
| 0 076 621 | 4/1983 | European Pat. Off. . |
| 0 199 630 | 10/1986 | European Pat. Off. . |
| 0 267 723 | 5/1988 | European Pat. Off. . |
| 0 337 549 | 10/1989 | European Pat. Off. . |
| 0 481 671 | 4/1992 | European Pat. Off. . |
| 0 525 973 | 2/1993 | European Pat. Off. . |
| 1 945 542 | 3/1971 | Germany . |
| 2 046 822 | 3/1972 | Germany . |
| 2 046 823 | 3/1972 | Germany . |
| 27 48 827 | 3/1978 | Germany . |
| 28 24 554 | 12/1978 | Germany . |
| 28 42 466 | 4/1979 | Germany . |
| 29 11 589 | 9/1979 | Germany . |
| 30 07 298 | 3/1981 | Germany . |
| 1192952 | 5/1970 | United Kingdom . |
| 1604752 | 12/1981 | United Kingdom . |
| 2093839 | 9/1982 | United Kingdom . |
| WO 93/00332 | 1/1993 | WIPO . |

OTHER PUBLICATIONS

Chem. Abstracts, vol. 115, No. 5, (Aug. 5, 1991) 41275e.

Firestone et al., Tetrahedron, vol. 46, No. 7, 2255–2262 (1990).

Chem. Abstracts, vol. 105, Abs. 97895t (1986).

D. D. Rees, et al., "Effects of Cystic Fibrosis Airway Secretions on the Rat Lung: The Role of Neutrophil Elastase", In press: American Journal Physiology: Lung Cellular and Molecular Physiology (1995).

D. S. Fletcher, et al., "An Inhibitor of Leukocyte Elastase Prevents Immune Complex–Mediated Hemorrhage in the Rat Lung", In press: Journal of Pharmacology & Experimental Therapeutics (1995).

D.S. Fletcher, et al., Am. Rev. Respir Dis, 141: 672–677 (1990).

Peitsch, Hartmut, Tetrahedron Letters, No. 45, pp. 4053–4056 (1976).

Tanaka, et al., Heterocycles, vol. 24, No. 9, pp. 2539–2543 (1986).

Bories, et al., Cell, vol. 59, pp. 959–968 (1989).

D. Campanelli, et al., J. Exp. Med., vol. 172, pp. 1709–1715 (1990).

G. Jenne, et al., Nature 346, 520 (1990).

Kao, et al., J. Clin. Invest. 82: 1963–1973 (1988).

Labbaye, et al., Proc. Natl. Acad. Sci. USA, vol. 88, pp. 9253–9256 (1991).

Shah, et al., J. Med. Chem., vol. 35, pp. 3745–3754 (1992).

Annals NY Acad. of Sci. Pulmonary Emphysema, vol. 624, (May 22, 1991) pp. 18–29, G.M. Turino, "Natural History and Clinical Management of Emphysema in Patients . . . ".

Annals NY Acad. of Sci. Pulmonary Emphysema, vol. 624, (May 22, 1991) pp. 45–59, G.L. Snider, et al., "Putative Role of Neutrophil Elastase in the Pathogenesis of Emphysema".

Annals NY Acad. of Sci. Pulmonary Emphysema, vol. 624, (May 22, 1991) pp. 81–86, J. Travis, et al., "Neutrophil Proteinases".

Annals NY Acad. of Sci. Pulmonary Emphysema, vol. 624, (May 22, 1991) pp. 97–108, J.A. Kramps, et al., "Role of Antileukoprotease in the Human Lung".

Annals NY Acad. of Sci. Pulmonary Emphysema, vol. 624, (May 22, 1991) pp. 167–187, R.A. Mumford, et al., "Direct Assay of Alpha (1–21), a PMN Elastase–Specific Cleavage Product of Fibrinogen . . . ".

Annals NY Acad. of Sci. Pulmonary Emphysema, vol. 624, (May 22, 1991) pp. 212–243, H.P. Schnebli, "Recombinant Elastase Inhibitors for Therapy".

Annals NY Acad. of Sci. Pulmonary Emphysema, vol. 624 (May 22, 1991) pp. 278–296, S.I. Rennard, et al., "Protease Injury in Airways Disease".

(List continued on next page.)

*Primary Examiner*—Phyllis G. Spivack

*Attorney, Agent, or Firm*—Valerie J. Camara; Mark R. Daniel

[57] ABSTRACT

Substituted azetidinones are herein disclosed for use in the treatment of various elastase-mediated diseases.

10 Claims, No Drawings

OTHER PUBLICATIONS

Physicians Desk Reference Edition 47, (1993), pp. 1672–1673, "Alpha 1–Proteinase Inhibitor (Human) Prolastin".

Am J. Respir. Crit. Care Med., vol. 150, pp. 207–213, (1994), P. Birrer, et al., "Protease–Antiprotease Imbalance in the Lungs of Children with Cystic Fibrosis".

S. Suter, et al., Am. Rev. Respir. Dis., vol. 140, pp. 1640–1644 (1989), "Relation between Tumor Necrosis Factor–alpha and Granulocyte Elastase–alpha1–Proteinase Inhibitor Complexes . . . ".

D. Rees, et al., Ped. Pulmon. Suppl. 9: 250, No. 178 (1993) "A Systemic Elastase Inhibitor Protects Rats Against Lung Injury from Instilled CF Sputum Sol".

J. B. Doherty, et al., Proc. Natl. Acad. Sci. USA, 90: 8727–8731 (Sep. 93).

W.A. Hanlon, et al., Journ. of Leukocyte Biology, 50: 43–48 (1991).

J. Stolk, et al., Am. J. Respir. Cell Mol. Biol, 6: 521–526 (1992).

SUBSTITUTED AZETIDIONES AS ANTI-INFLAMMATORY AND ANTIDEGENERATIVE AGENTS

RELATED APPLICATION DATA

This is a continuation of application Ser. No. 08/416,771 filed on Apr. 13, 1995, abandoned. This is a National Filing of International application number PCT/US93/10268 filed Oct. 26, 1993.

BACKGROUND OF THE INVENTION

We have found that a group of new substituted azetidinones are potent elastase inhibitors and therefore are useful anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, chronic bronchitis, glomerulonephritis, osteoarthritis, spondylitis, lupus, psoriasis, atherosclerosis, sepsis, septicemia, shock, myocardial infarction, reperfusion injury, periodontitis, cystic fibrosis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am. Jul.* 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/ pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, E. Holzer and H. Tschesche, eds. Springer-Verlag, Berlin, Heidelberg, New York, pp. 196–206, 1979.

In a second aspect this invention concerns the use of novel azetidinones in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation. We have found that the substituted azetidinones disclosed herein are inhibitors of proteinase 3 (PR-3), also known as myeloblastin.

See C. Labbaye, et al., Proc. Natl. Acad. Sci. USA, vol. 88, 9253–9256, (1991), Wegner autoantigen and myeloblastin are encoded by a single mRNA; D. Campanelli, et al., J. Exp. Med., vol. 172, 1709–1714, (1990), Cloning of cDNA for proteinase 3: A serine protease, antibiotic, and autoantigen from human neutrophils; and Bories, et. al., Cell vol. 59, 959–968, (1989) Down-regulation of a serine protease, myeloblastin, causes growth arrest and differentiation of promyelocytic leukemia cells.

Recently, down regulation of PR-3 has been implicated in the proliferation and maintenance of a differentiated state of certain leukemia cells. In particular, Bories, et. al., have shown that expression of this enzyme, hereinafter designated proteinase 3/myeloblastin, can be inhibited by treatment of HL-60 human leukemia cells with an antisense oligodeoxynucleotide and that such treatment induces differentiation and inhibits proliferation of these cells. Moreover, we have now demonstrated that the treatment of the HL-60 cell human leukemia cell line, among others, with the compounds of the instant invention, likewise results in the inhibition of proliferation and induction of differentiation in such cells.

Accordingly, we believe that treatment of leukemia such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation, comprising: administration of a therapeutically effective amount of compound of Formula I will result in remission of the disease state. Administration may be either oral or parenteral.

BRIEF DESCRIPTION OF THE INVENTION

The instantly claimed invention is directed to specifically substituted azetidinones of Formula I

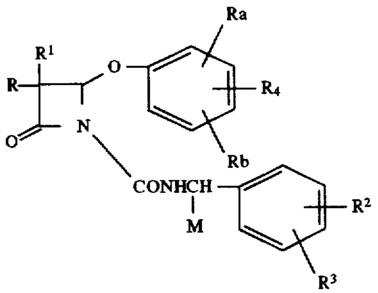

These substituted azetidinones have been found to be useful anti-inflammatory and antidegenerative agents. This invention is also directed to pharmaceutical compositions and methods of using these specifically substituted azetidinones. These compounds will also be useful in the treatment of certain leukemias and leukemia related conditions.

DETAILED DESCRIPTION OF THE INVENTION

This invention relates to potent elastase inhibitors of Formula (I),

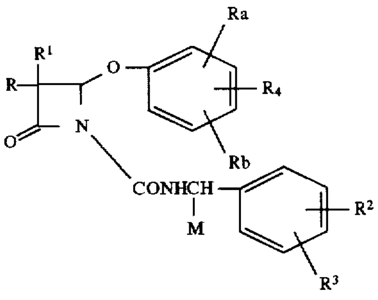

which are useful in the prevention, control and treatment of inflammatory and degenerative conditions especially arthritis and emphysema.

More particularly, the instant invention is directed to the compounds of the Formula (I)

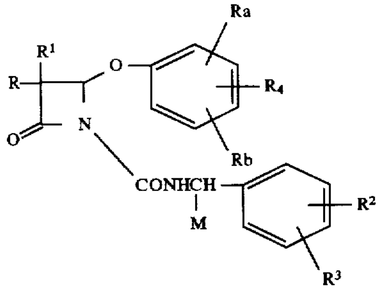

and pharmaceutically acceptable salts thereof wherein:

R is $C_{1-6}$alkyl;

$R^1$ is $C_{1-6}$alkyl or $C_{1-6}$alkoxy-$C_{1-6}$alkyl;

M is
(1) hydrogen,
(2) $C_{1-6}$alkyl,
(3) hydroxy $C_{1-6}$alkyl,
(4) halo $C_{1-6}$alkyl,
(5) $C_{2-6}$alkenyl, or
(6) $C_{1-6}$alkoxy-$C_{1-6}$alkyl;

Ra and Rb are each individually
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) di-($C_{1-6}$alkyl)amino;
(9) hydroxy;

$R^2$ and $R^3$ are each independently
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino$C_{2-3}$alkyloxy carbonyl wherein the amino is optionally mono or di substituted with $C_{1-6}$alkyl,
(9) amino$C_{2-3}$alkylamino carbonyl wherein the amino is optionally mono or di substituted with $C_{1-6}$alkyl,
(10) hydroxy,
(11) aminocarbonyl wherein the amino is optionally mono or di substituted with $C_{1-6}$alkyl,

(12) hydroxymethyl,

(13) aminocarbonyloxy $C_{1-3}$alkyloxy wherein the amino is optionally mono or di substituted with $C_{1-6}$alkyl,

(14) cyano,

(15) morpholinocarbonylphenyl,

(16) amino wherein the amino is optionally mono or di substituted with $C_{1-6}$alkyl, with the proviso that $R^2$ and $R^3$ may be joined together to form a methylenedioxy group or a furan ring,

(17) morpholinocarbonyl;

(a) 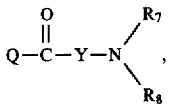 , or (b) 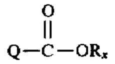

wgere $R_x$ is carboxy benzyloxycarbonyl$C_{1-3}$alkyl, or t-butoxycarbonyl$C_{1-3}$alkyl, wherein Q is a covalent bond or

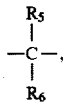

wherein $R_5$ and $R_6$ are each individually $C_{1-3}$alkyl or hydrogen,

Y is 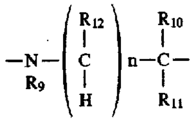

or

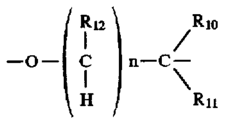

or a covalent bond;

$R_{12}$ is hydrogen or $C_{1-3}$alkyl;

$R_7$ and $R_8$ are each individually (a) hydrogen, (b) $C_{1-6}$alkyl, (c) $C_{1-6}$alkyloxy $C_{2-3}$alkyl, (d) hydroxy $C_{2-6}$alkyl, (e) polyhydroxy$C_{2-6}$alkyl, (f) carboxamido $C_{1-6}$alkyl, (g) polyacyloxy$C_{2-6}$alkyl (h) $C_{1-6}$alkanoyl, (i) substituted phenyl or phenyl $C_{1-6}$alkyl, wherein the substitutent is $X_1$ as defined immediately below, (j) $C_{2-6}$alkenyl, (k) $C_{6-10}$cycloalkenyl, (1) heteroaryl $C_{1-6}$alkyl wherein the hetero aryl includes pyridinyl, imidazolyl, triazolyl, benzylimidazolyl, and furyl, (m) carboxy $C_{1-6}$alkyl, (n) carbo $C_{1-6}$alkoxy $C_{1-3}$alkyl, (o) phenylsulfonyl, (p) $C_{1-6}$alkylsulfonyl, (q) benzyloxy, (r) morpholinyl $C_{1-3}$alkylsulfonyl, (s) tetrahydropyranyl, (t) amino$C_{1-3}$alkylsulfonyl wherein the amino is optionally mono or di substituted with $C_{1-6}$alkyl, (u) aminocarbonyl wherein the amino is optionally mono or di substituted with $C_{1-6}$alkyl, (v) aminocarbonyloxy$C_{2-6}$alkyl wherein the amino is optionally mono or di substituted with $C_{1-6}$alkyl, (w) azabicyclo of 7 to 12 atoms, (x) di $C_{1-3}$alkylamino $C_{2-6}$alkyl wherein the amino is optionally mono or di substituted with $C_{1-6}$alkyl, (y) bicycloalkyl of 7 to 12 atoms, (z) $C_{3-10}$cycloalkyl optionally substituted with $C_{1-6}$alkyl, (aa) pyrazolidinyl, (bb) substituted piperidinyl or prrolidinyl wherein the substitutent is hydrogen, $C_{1-3}$alkyl, hydroxy$C_{1-3}$alkylbenzyl, carboxamido or amino wherein the amino is optionally mono or di substituted with $C_{1-6}$alkyl, (cc) substituted pyrrolidinyl wherein the substitutent is carboxamido or amino wherein the amino is optionally mono or di substituted with $C_{1-6}$alkyl, (dd) pyrimidinyl, (ee) N-cyano-N'-phenylamidino, (ff) phosphono$C_{1-6}$alkyl, or (gg) α-$C_{1-3}$alkyl benzyl or mono or di substituted benzyl or mono or di substituted pyridylmethyl, wherein the substitutents are $X_1$ and $X_2$, wherein $X_1$ is (1) hydrogen, (2) halo, (3) $C_{1-6}$alkyl, (4) halo-$C_{1-6}$alkyl, (5) $C_{2-6}$alkenyl, (6) hydroxy-$C_{1-6}$alkyl, (7) $C_{1-6}$alkylcarbonyl, (8) $C_{1-6}$alkylcarbonylamino;

(9) CN,

(10) $CF_3$,

(11) $CH_3O$,

(12) amino wherein the amino is optionally mono or di substituted with $C_{1-6}$alkyl;

(13) carboxy, or

(14) phenylsulfonylaminocarbonyl;

$X_2$ is hydrogen, halo or $C_{1-6}$alkyl;

n is 1, 2, 3, 4 or 5;

$R_9$ is selected from hydrogen, $C_{14}$ alkyl, and $C_{1-3}$alkoxy$C_{1-3}$alkyl; or phenyl, phenyl $C_{1-3}$alkyl, pyridyl, and pyridyl $C_{1-3}$alkyl;

$R_{10}$ and $R_{11}$ are each independently selected from hydrogen, $C_{1-4}$alkyl, and $C_{1-3}$alkoxy $C_{1-3}$alkyl, or aryl as defined above, or are together O=; or wherein $R_7$ and $R_8$ are joined together to form mono or di substituted ring of 4, 5, 6, or 7 atoms or 7 to 12 atoms such as (1) piperidinyl or homopiperdinyl, (2) piperazinyl, (3) morpholinyl, thiomorpholinyl or 1,1-dioxo-4-thiomorpholinyl, (4) pyrroylidinyl, (5) pyrryl, (6) imidazolyl,
(7) triazolyl,
(8) saturated azabicyclo of 7 to 12 atoms,
(9) azaspiro having 3 to 9 carbon atoms, said ring being saturated,
(10) tetrazolyl,
(11) pyrazolidinyl,
(12) dihydodimethozyisoquinolyl,
(13) azetidinyl, or
(14) diazabicyclo ring of 7–12 atoms, wherein the substituents are each selected from the group consisting of hydrogen and $C_{1-3}$alkyl, benzyloxycarbonyl, carboxy, phenyl $C_{1-3}$alkyl amino carbonyl, pyrrolidinylmethyl, hydroxy $C_{1-3}$alkyl, $C_{1-6}$alkyloxy, $C_{1-4}$alkyloxy carbonyl, aminocarbonyl wherein the amino is optionally mono or di substituted with $C_{1-6}$alkyl, and oxo; or —N(R7)R8 may be an amino acid residue including natural amino acids such as lysine; or $R_8$ and $R_9$ are joined together to form a mono or di substituted saturated monocyclic ring of 6 to 7 atoms and having two hetero atoms which are the nitrogens to which $R_8$ and $R_9$ are attached; said rings to include piperazinyl and homopiperazinyl; or $R_9$ and $R_{10}$ are joined together to form a mono or di substituted monocyclic saturated ring of 5 to 7 atoms and having one hetero atom which is the nitrogen to which $R_9$ is attached; or wherein $R_9$ and $R_{12}$ are joined together to form a mono or di substituted saturated monocyclic ring of 5, 6; or 7 atoms, said ring having one hetero atom which is the nitrogen to which $R_9$ is attached; or wherein $R_{10}$ and $R_{12}$ are joined together to form a mono or di substituted saturated monocyclic ring of 5, 6, or 7 carbon atoms; or wherein $R_8$ and $R_{11}$ are joined together to form a mono or di substituted saturated monocyclic ring of 5, 6, or 7 atoms, said ring having one hetero atom which is the nitrogen to which $R_8$ is attached; and the substituents are independently selected from Hydrogen and C1-3alkyl.

As appreciated by those of Skill in the art the term "alkyl" such as in $C_{1-6}$alkyl, includes, methyl, ethyl, propyl, butyl, pentyl, and hexyl, and where appropriate, branched chained forms including isopropyl and tert-butyl.

As may also be appreciated by those of skill in the art, the

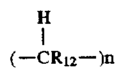

spacer in definition Y, may, in the alternative be placed to the right of $CR_{10}R_{11}$.

As may also be appreciated, the group

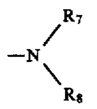

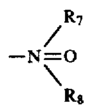

may also be oxidized to the corresponding oxide

In one Class the instant invention is directed to the compounds of the Formula (I)

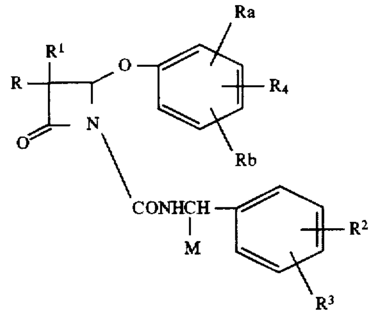

and pharmaceutically acceptable salts thereof wherein:

R is $C_{1-6}$alkyl;

$R^1$ is $C_{1-6}$alkyl or $C_{1-6}$alkoxy-$C_{1-6}$alkyl;

M is
(1) hydrogen,
(2) $C_{1-6}$alkyl,
(3) hydroxy $C_{1-6}$alkyl,
(4) halo $C_{1-6}$alkyl,
(5) $C_{2-6}$alkenyl, or
(6) $C_{1-6}$alkoxy-$C_{1-6}$alkyl;

Ra is
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino wherein the amino is optionally mono or di substituted with $C_{1-6}$alkyl;

Rb is hydrogen, or $C_{1-6}$alkyl, $R^2$ and $R^3$ are each independently
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino wherein the amino is optionally mono or di substituted with $C_{1-6}$alkyl, or with the proviso that $R^2$ and $R^3$ may be joined together to form a methylenedioxy group or a furan ring;

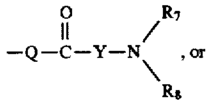

, or (a)

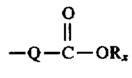

(b)

where $R_x$ is carboxy$C_{1-6}$alkyl, benzyloxycarbonyl$C_{1-3}$alkyl, or t-butoxycarbonyl$C_{1-3}$alkyl, wherein Q is a covalent bond or

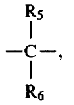

wherein $R_5$ and $R_6$ are each individually $C_{1-3}$alkyl or hydrogen

Y is 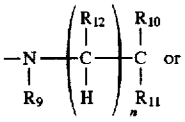 or

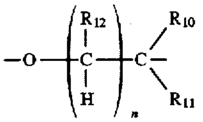

or a covalent bond;

$R_{12}$ is hydrogen or $C_{1-3}$alkyl;

$R_7$ and $R_8$ are each individually (a) hydrogen, (b) $C_{1-6}$alkyl, (c) $C_{1-6}$alkyloxy $C_{2-3}$alkyl, (d) hydroxy $C_{2-6}$alkyl, (e) carboxamido $C_{1-6}$alkyl, (f) $C_{1-6}$alkanoyl, (g) substituted phenyl or phenyl $C_{1-6}$alkyl wherein the substitutents are $X_1$, and $X_2$ (h) $C_{2-6}$alkenyl, (i) $C_{6-10}$cycloalkenyl, (j) heteroaryl $C_{1-6}$alkyl wherein the hetero aryl includes pyridinyl, imidazolyl, triazolyl, benzylimidazolyl, and furyl, (k) carboxy $C_{1-6}$alkyl, (l) $C_{1-6}$alkylsulfonyl, (m) carbo$C_{1-6}$alkyloxy$C_{2-3}$alkyl, (n) morpholinyl $C_{1-3}$alkylsulfonyl, (o) amino$C_{1-3}$alkylsulfonyl wherein the amino is optionally mono or di substituted with $C_{1-6}$alkyl, (p) aminocarbonyl wherein the amino is optionally mono or di substituted with $C_{1-6}$alkyl, (q) aminocarbonyloxy$C_{1-6}$alkyl wherein the amino is optionally mono or di substituted with $C_{1-6}$alkyl, (r) di $C_{1-3}$alkylamino $C_{1-6}$alkyl wherein the amino is optionally mono or di substituted with $C_{1-6}$alkyl, (s) pyrazolidinyl, (t) substituted piperidinyl as defined above, (u) substituted pyrrolidinyl as defined above, (v) pyrimidinyl, (w) benzyloxy, (x) $C_{3-10}$cycloalkyl, (z) α-$C_{1-3}$alkyl benzyl or mono or di substituted benzyl or mono or di substituted pyridylmethyl, wherein the substitutents are $X_1$ and $X_2$, wherein $X_1$ is (1) hydrogen, (2) halo, (3) $C_{1-6}$alkyl, (4) halo-$C_{1-6}$alkyl, (5) $C_{2-6}$alkenyl, (6) hydroxy-$C_{1-6}$alkyl, (7) $C_{1-6}$alkylcarbonyl, (8) $C_{1-6}$alkylcarbonylamino;

(9) di-$C_{1-3}$alkylamino; or

(10) carboxy, $X_2$ is hydrogen, halo or $C_{1-6}$alkyl;

n is 1, 2, 3, 4 or 5;

$R_9$ is selected from hydrogen, $C_{1-4}$ alkyl, and $C_{1-3}$alkoxy$C_{1-3}$alkyl; $R_{10}$ and $R_{11}$ are each independently selected from hydrogen, $C_{1-4}$alkyl, and $C_{1-3}$alkoxy $C_{1-3}$alkyl; or wherein $R_7$ and $R_8$ are joined together to form mono or di substituted ring of 4, 5, 6, or 7 atoms such as (1) piperidinyl, (2) piperazinyl, (3) morpholinyl, (4) pyrroylidinyl, (5) pyrryl, (6) imidazolyl, (7) triazolyl, (8) tetrazolyl, (9) pyrazolidinyl,

(10) azetidinyl, wherein the substituents are each selected from the group consisting of hydrogen and $C_{1-3}$alkyl, benzyloxycarbonyl, carboxy, phenyl $C_{1-3}$alkyl amino carbonyl, pyrrolidinyl, methyl, hydroxy $C_{1-3}$alkyl, $C_{1-6}$alkyloxy, $C_{1-4}$alkyloxy carbonyl, and oxo; or $R_8$ and $R_9$ are joined together to form a saturated ring of 5 to 7 atoms and having two hetero atoms; or $R_9$ and $R_{10}$ are joined together to form a saturated ring of 5 to 7 atoms and having one hetero atom; or wherein $R_9$ and $R_{12}$ are joined together to form a ring of 5, 6, or 7 atoms, said ring being saturated; or wherein $R_{10}$ and $R_{12}$ are joined together to form a ring of 5, 6, or 7 atoms, said ring being saturated; or wherein $R_8$ and $R_{11}$ are joined together to form a ring of 5, 6, or 7 atoms, said ring being saturated and having one hetero atom.

In one subclass, the invention concerns compounds of Formula I wherein

R is $C_{1-3}$alkyl;

$R_1$ is $C_{1-3}$alkyl;

M is (a) $C_{1-6}$alkyl, or (b) $C_{2-6}$alkenyl;

$R^2$ is (a) hydrogen, (b) $C_{1-6}$alkyl, or $C_{1-6}$alkoxy, and $R^3$ is hydrogen, or $R^2$ and $R^3$ are joined together to form a methylenedioxy group or a furan ring;

$R_5$ and $R_6$ are each individually hydrogen or $C_{1-3}$alkyl;

$R_7$ and $R_8$ are each independently selected from (a) hydrogen, (b) $C_{1-3}$alkyl, (c) $C_{1-3}$alkoxy $C_{2-3}$alkyl, (d) $C_{3-7}$cycloalkyl, (e) hydroxy$C_{2-3}$alkyl, (d) carbo $C_{1-4}$alkyloxymethyl, (g) substituted benzyl wherein the substituents are $X_1$ and $X_2$ wherein $X_1$ is hydrogen and $X_2$ is (1) hydrogen, (2) halo, or (3) $C_{1-3}$alkyl;

n is 1, 2 or 3, and $R_9$, $R_{10}$ and $R_{11}$ are each independently selected from hydrogen, $C_{1-4}$alkyl, and $C_{1-3}$alkoxy $C_{1-3}$alkyl; or $R_7$ and $R_8$ are joined together to form a substituted ring selected from (a) piperidinyl, (b) piperazinyl, and (c) morpholinyl;

or $R_8$ and $R_9$ are joined together to form a ring of 6 to 7 atoms and having two hetero atoms; $R_9$ and $R_{10}$ are joined together to form a saturated ring of 5 to 7 atoms and having one hetero atom; or wherein $R_9$ and $R_{12}$ are joined together to form a ring of 5, 6, or 7 atoms, said ring being saturated; or wherein $R_{10}$ and $R_{12}$ are joined together to form a ring of 5, 6, or 7 atoms, said ring being saturated; or wherein $R_8$ and $R_{11}$ are joined together to form a ring of 5, 6, or 7 atoms, said ring being saturated and having one hetero atom.

In a narrower sub-class are the compounds wherein

Q is a covalent bond;

R is methyl or ethyl;

$R_1$ is methyl or ethyl;

M is (a) $C_{1-4}$alkyl, or (b) $C_{2-3}$alkenyl;

$R^2$ is (a) hydrogen, (b) $C_{1-3}$alkyl, or $C_{1-3}$alkoxy, and $R^3$ is hydrogen, or $R^2$ and $R^3$ are joined together to form a furan or dioxacyclopentane ring;

n is 1 or 2;

$R_9$ and $R_{10}$ are each independently selected from (a) $C_{1-3}$alkyl, (b) $C_{1-3}$alkoxy $C_{1-3}$alkyl, (c) hydrogen, $R_7$ and $R_8$ are each independently selected from (a) $C_{1-3}$alkyl, (b) $C_{1-3}$alkoxy $C_{2-3}$alkyl, (c) hydrogen, (d) hydroxyethyl, (e) carboethoxymethyl, (f) cyclopropyl, or $R_7$ and $R_8$ are joined together to form a substituted ring selected from (a) piperidinyl, and (b) morpholinyl, or $R_8$ and $R_9$ are joined together to form a piperazine ring.

As is defined above, various rings are formed when R8, R9, R10 and R12 are joined. The following is a non-limiting description of some of the preferred rings that are formed when these various substituents are joined.

R8 and R9 are joined

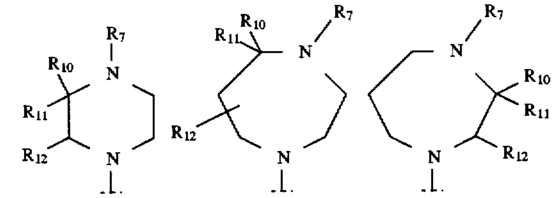

R9 and R10 are joined

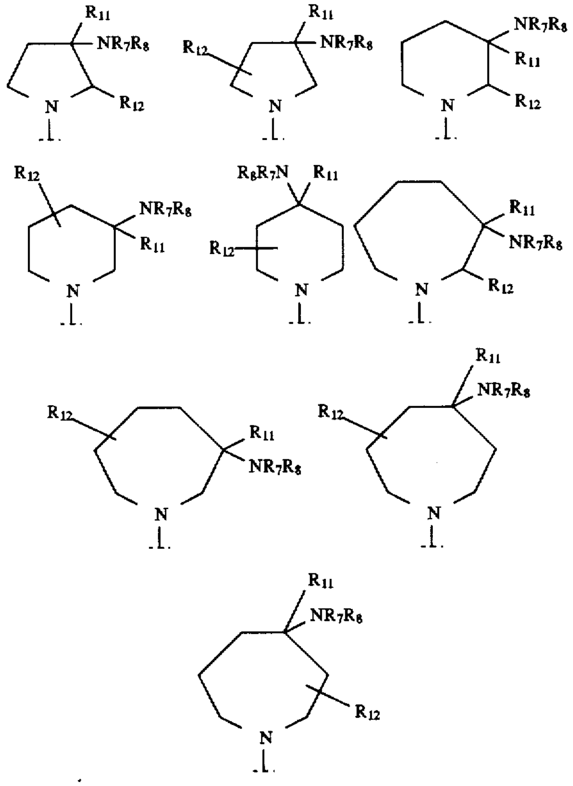

R9 and R12 are joined

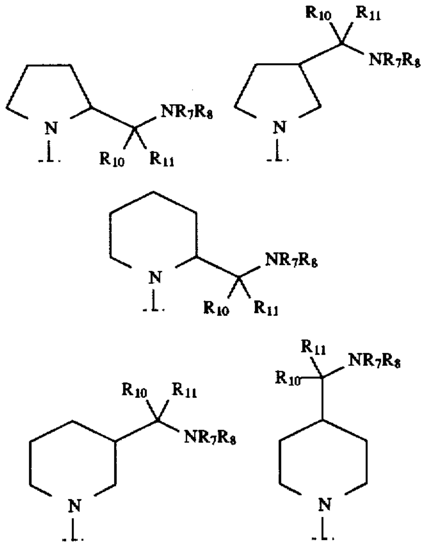

-continued

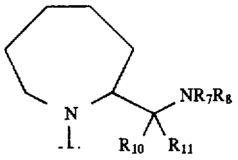

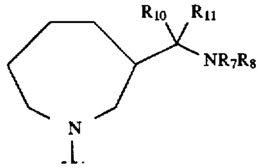

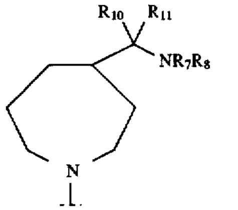

R10 and R12 are joined

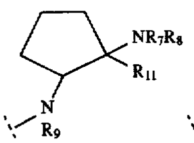

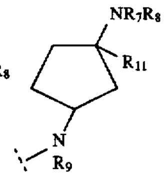

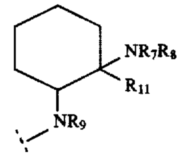

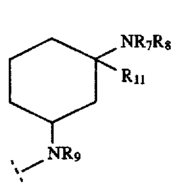

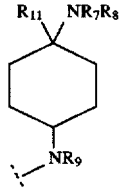

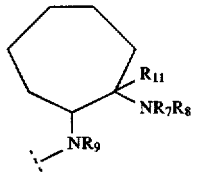

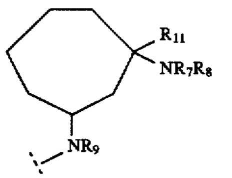

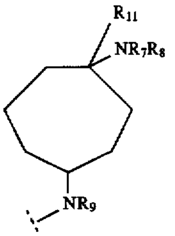

R10 and R12 are joined

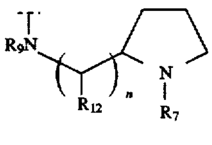

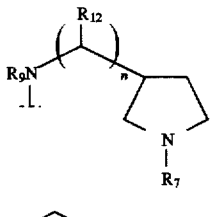

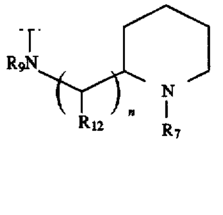

-continued

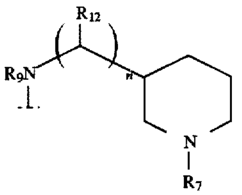

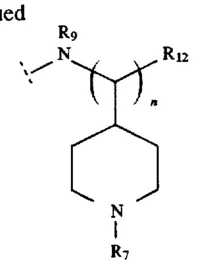

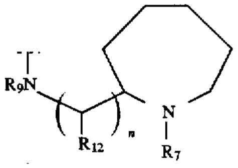

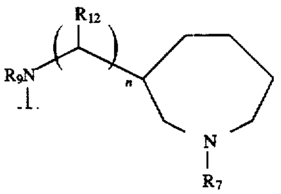

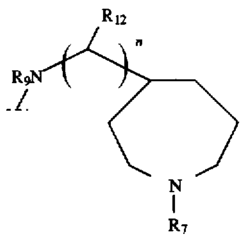

In another aspect the present invention is directed to the treatment of leukemia, such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation with compounds of Formula I.

Treatment of leukemia cells comprises: administration of a therapeutically effective amount of a compound of Formula I results in the inhibition of proteinase 3/myeloblastin, inhibition of elastase, inhibition of proliferation of the leukemia cells, induction of differentiation of the leukemia cells, and remission of the disease state.

In one alternative embodiment the invention concerns a method of treating leukemia comprising:

administration to a patient in need of such treatment of a therapeutically effective amount of compound of Formula I.

In a second alternative embodiment the invention concerns a method of inhibiting proteinase 3/myeloblastin, comprising:

administration to a patient in need of such inhibition of a therapeutically effective amount of compound of Formula I as defined above.

In a third alternative embodiment the invention concerns a method of inhibiting proteinase 3/myeloblastin and elastase, comprising:

administration to a patient in need of such inhibition of a therapeutically effective amount of compound of Formula I as or a pharmaceutically acceptable salt thereof as defined above.

In a fourth embodiment the invention concerns a method of inducing cellular differentiation in leukemia cells comprising:

administration to a patient in need of such inhibition of a therapeutically effective amount of compound of Formula I or a pharmaceutically acceptable salt thereof as defined above.

Each of the above alternative embodiments (i.e., those relating to PR3 or cancer), also concerns co-administration of a compound of Formula I as defined above, with an agent or agents known in the art for treatment of leukemia, including, but not limited to epsilon-aminocaproic acid, heparin, trasylol (aprotinin); prednisolone; cytosine arabinoside; β-mercaptopurine; cytarabine; an anthracycline (see Young et. al. (1981) N. Engl. J. Med. 305:139) such as daunorubicin, doxorubicin and epidoxorubicin; Vitamin A derivatives including retinoids and all-trans-retinoic acid (See Ellison R. R. et.al. (1968) *Blood* 32:507, Arabinosyl Cytosine: A useful agent in the treatment of leukemia in adults; Cytarabine: Therapeutic new dimensions, Semin. Oncol. 12:1 (1985, supp 3); Weinstein H. J. et. al. (1983) *Blood* 62:315, Chemotherapy for acute myelogenous leukemia in children and adults results in an enhanced therapeutic response.

Accordingly, in a fifth alternative embodiment the invention concerns a pharmaceutical composition comprising:

a pharmaceutical carrier, a therapeutically effective amount of compound selected from the group consisting of epsilon-aminocaproic acid, heparin, trasylol, prednisolone, cytosine arabinoside, β-mercaptopurine, cytarabine, an anthracycline and a vitamin A derivative; and a therapeutically effective amount of compound of Formula I as defined above.

In a sixth alternative embodiment the invention concerns a method of treating leukemia comprising:

co-administration to a patient in need of such treatment of a therepeutically effective amount of compound selected from the group consisting of epsilon-aminocaproic acid, heparin, trasylol, prednisolone, cytosine arabinoside, b-mercaptopurine, cytarabine, an anthracycline, and a vitamin A derivative; and a therapeutically effective amount of compound of Formula I as defined above.

In a seventh alternative embodiment the invention concerns a method of inhibiting proteinase 3/myeloblastin, comprising:

co-administration to a patient in need of such inhibition of a therapeutically effective amount of compound selected from the group consisting of epsilon-aminocaproic acid, heparin, trasylol, prednisolone, cytosine arabinoside, β-mercaptopurine, cytarabine, an anthracycline, and a vitamin A derivative; and a therapeutically effective amount of compound of Formula I as defined above.

In an eighth alternative embodiment the invention concerns a method of inhibiting proteinase 3/myeloblastin and elastase, comprising:

administration to a patient in need of such inhibition of a therapeutically effective amount of compound selected from the group consisting of epsilon-aminocaproic acid, heparin, trasylol, prednisolone, cytosine arabinoside, β-mercaptopurine, cytarabine, an anthracycline, and a vitamin A derivative; and a therapeutically effective amount of compound of Formula I as defined above.

In a ninth alternative embodiment the invention concerns a method of inducing cell differentiation in leukemia cells comprising:

administration to a patient in need of such inducing of a therapeutically effective amount of compound selected from the group consisting of epsilon-amino-caproic acid, heparin, trasylol, prednisolone, cytosine arabinoside, β-mercaptopurine, cytarabine, an anthracycline and a vitamin A derivative; and a therapeutically effective amount of compound of Formula I as defined above.

In a tenth alternative embodiment of the invention the instant compounds can also be used in the treatment of diseases associated with over-expression of cDNa, such as those pulmonary diseases is with abnormal, viscous, or inspissated purulent secretions. Such conditions are found in acute or chronic bronchopulmonary disease including infectious pneumonia, bronchitis or tracheobronchitis, bronchiectasis, cystic fibrosis, asthma, tuberculosis or fungal infections. Utility is also found in atelactasis due to tracheal or btonchial impaction and complications of tracheostomy.

In addition, the instant compounds can be co-administered with cDNase which also finds utility in these pulmonary diseases, and which is described in WO 90/07572.

The compounds of the invention are prepared by known methods or are prepared among other methods by the following representative schemes. For example, methods for making such compounds are disclosed in EP 0 337 549, published Oct. 18, 1989, which is hereby incorporated by reference.

This invention also relates to a method of treating inflammation in patients using a compound of Formula (I), particularly a preferred compound as the active constituent.

It has been found that the following compound are effective inhibitors of the proteolytic function of human neutrophil elastase as shown below in Table 1 to 10.

TABLE 1

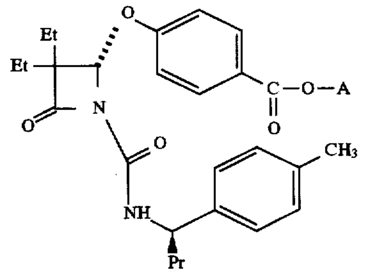

| No. | A | Kobs/[I] |
|---|---|---|
| 1 | $-CH_2CH_2N(CH_3)_2$ | 1,566,000 |
| 2 | $-CH_2CO_2H$ | 1,667,000 |
| 3 | $-CH_2-C(O)N(CH_2CH_2OH)_2$ | 3,428,000 |
| 4 | $-CH_2-C(O)N(CH_3)CH_2C(O)NH_2$ | 4,293,000 |
| 5 | $-CH_2C(O)NH-C(CH_2OH)_3$ | 4,448,000 |
| 6 | $-CH_2C(O)N(CH_3)_2$ | 2,997,000 |
| 7 | $-CH_2CH_2N(CH_3)Ac$ | 1,558,000 |
| 8 | $-CH_2C(O)$-Pro-$OCH_2Ph$ | 12,501,000 |
| 9 | $-CH_2C(O)$-Pro-OH | 1,571,000 |
| 10 | $-CH(CH_3)CO_2CH_2Ph$ | 2,891,000 |
| 11 | $-CH(CH_3)CO_2H$ | 1,132,000 |
| 12 | $-CH(CH_3)C(O)N(Et)_2$ | 2,815,000 |
| 13 | $-CH(CH_3)CH_2N(CH_3)_2$ | 2,472,000 |
| 14 | $-CH_2CH_2CH_2N(CH_3)_2$ | 2,855,000 |
| 15 | $-CH_2CH_2N(O)(CH_3)_2$ | 2,162,000 |
| 16 | $-CH_2CH_2N(Et)_2$ | 2,291,000 |
| 17 | $-CH_2CH_2$(4-morpholinyl) | 4,733,000 |
| 18 | $-CH_2CH_2CH_2CH_2N(CH_3)_2$ | 1,934,000 |
| 19 | $-CH_2C(O)$-Pro-$NHCH_2Ph$ | 4,956,000 |
| 20 | $-CH_2C(CH_3)_2N(CH_3)_2$ | 1,470,000 |
| 21 | $-CH_2CH_2N(i\text{-}Pr)_2$ | 1,671,000 |
| 22 | $-CH_2CH_2$(4-carbobenzyloxy-1-piperazinyl) | 4,115,000 |
| 23 | $-CH_2CH_2N(n\text{-}Bu)_2$ | 992,000 |
| 24 | $-CH_2CH_2CH_2CH_2CH_2CH_2N(CH_3)_2$ | 1,988,000 |

TABLE 1-continued

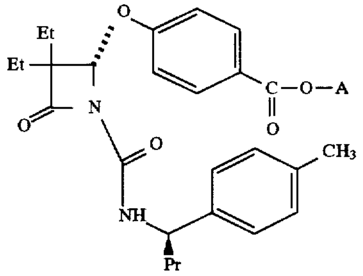

| No. | A | Kobs/[I] |
|---|---|---|
| 25 | $-CH_2CH_2$(1-piperazinyl) | 1,709,000 |
| 26 | $-CH_2CH_2$(4-methyl-1-piperazinyl) | 4,685,000 |
| 27 | $-CH_2CH_2$(4-acetyl-1-piperazinyl) | 3,262,000 |
| 28 | $-CH_2CH_2N(Ph)_2$ | 188,000 |
| 29 | $-CH_2CH_2N(CH_2CH{=}CH_2)_2$ | 891,000 |
| 30 | $-CH_2CH(Ph)N(CH_3)_2$ | 656,000 |
| 31 | $-CH_2CH_2N(CH_3)CH_2Ph$ | 1,180,000 |

TABLE 2

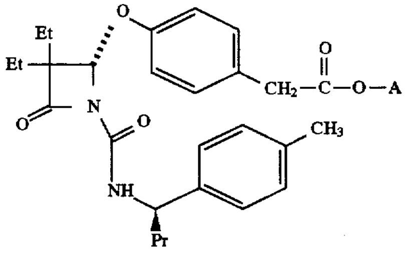

| No. | A | Kobs/[I] |
|---|---|---|
| 32 | $-CH_2CH_2N(CH_3)_2$ | 1,993,000 |
| 33 | $-CH_2CH_2CH_2N(CH_3)_2$ | 1,151,000 |
| 34 | $-CH_2CH_2N(Et)_2$ | 1,339,000 |
| 35 | $-CH_2CH_2$-(4-morpholinyl) | 1,725,000 |
| 36 | $-CH(CH_3)CH_2N(CH_3)_2$ | 1,688,000 |
| 37 | $-CH_2-C(CH_3)_2N(CH_3)_2$ | 2,100,000 |
| 38 | $-CH_2CO_2H$ | 1,008,000 |
| 39 | $-CH_2CH_2N(CH_3)CH_2Ph$ | 751,000 |

TABLE 3

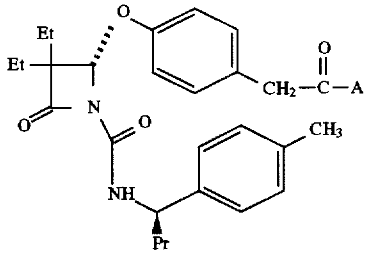

| No. | A | Kobs/[I] |
|---|---|---|
| 40 | $-N(CH_2CH_2OH)_2$ | 1,241,000 |
| 41 | 4-methyl-1-piperazinyl | 974,000 |
| 42 | 4-morpholinyl | 1,088,000 |
| 43 | $-NHCH_2CH_2N(CH_3)_2$ | 1,211,000 |
| 44 | $-N(CH_3)CH_2CH_2N(CH_3)_2$ | 1,243,000 |
| 45 | $-NHCH_2CH_2CH_2N(CH_3)_2$ | 1,118,000 |
| 46 | $-NHCH_2CH_2$-(4-pyridyl) | 2,254,000 |
| 47 | $-NHCH_2CO_2H$ | 876,000 |
| 48 | $-NHCH(CH_3)CO_2H$ | 676,000 |
| 49 | $-NHCH_2C(O)N(CH_2CH_2OH)_2$ | 1,295,000 |
| 50 | $-N(CH_3)CH_2CO_2H$ | 989,000 |
| 51 | $-NHCH(CH_3)C(O)N(CH_2CH_2OH)_2$ | 939,000 |
| 52 | $-N(CH_3)CH_2C(O)N(CH_2CH_2OH)_2$ | 273,000 |
| 53 | $-N(CH_3)CH_2CH_2$-(4-morpholinyl) | 2,511,000 |
| 54 | $-N(CH_3)CH_2CH_2N(CH_2CH_2OCH_3)_2$ | 1,388,000 |
| 55 | $-N(CH_3)CH_2CH_2N(Et)_2$ | 1,316,000 |
| 56 | $-N(CH_3)CH_2CH_2CH_2N(CH_3)_2$ | 1,047,000 |
| 57 | $-NHCH_2CH(CH_3)N(CH_3)_2$ | 1,344,000 |
| 58 | $-N(CH_3)CH_2CH_2N(i\text{-}Pr)_2$ | 1,634,000 |
| 59 | $-N(n\text{-}Pr)_2$ | 1,144,000 |
| 60 | $-N(Et)_2$ | 1,079,000 |
| 61 | 3-chloroanilino- | 733,000 |
| 62 | 3-methoxyanilino- | 1,621,000 |
| 63 | 4-fluoroanilino- | |
| 64 | $-N(CH_3)CH_2CH_2CH_2CO_2H$ | 917,000 |
| 65 | $-N(CH_3)CH_2CH_2CH_2C(O)NHSO_2Ph$ | 1,335,000 |
| 66 | $-N(CH_3)CH_2CH_2CH_2N(CH_3)CH_2Ph$ | 1,355,000 |
| 67 | $-N(CH_3)_2$ | 942,000 |
| 68 | $-N(CH_3)CH_2Ph$ | 1,897,000 |
| 69 | $-N(CH_3)CH_2CH_2N(CH_3)CH_2Ph$ | 2,792,000 |
| 70 | $-NH-O-CH_2Ph$ | 2,371,000 |
| 71 | $-N(CH_3)$(4-carboxyphenyl) | 1,508,000 |
| 72 | $-N(CH_3)$(4-benzenesulfonyl-amino-carbonyl-phenyl) | 3,284,000 |

TABLE 4

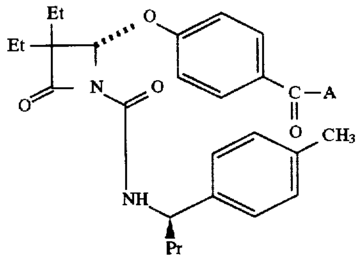

| No. | A | Kobs/[I] |
|---|---|---|
| 73 | $-NHCH_2CH_2N(CH_3)_2$ | 968,000 |
| 74 | $-NH-CH_2CO_2H$ | 1,434,000 |
| 75 | $-N(CH_3)CH_2CH_2N(CH_3)_2$ | 1,916,000 |
| 76 | $-N(Et)CH_2CH_2N(CH_3)_2$ | 1,436,000 |
| 77 | $-NHCH_2CH_2N(Et)_2$ | 1,187,000 |
| 78 | $-NHCH_2CH_2$-(4-morpholinyl) | 1,841,000 |
| 79 | $-N(CH_3)CH_2CH_2$-(4-morpholinyl) | 2,118,000 |
| 80 | $-N(CH_3)CH_2CH_2N(CH_2CH_2OCH_3)_2$ | 2,078,000 |
| 81 | $-N(CH_3)CH_2CH_2N(Et)_2$ | 2,191,000 |
| 82 | $-N(Ph)CH_2CH_2N(CH_3)_2$ | 2,504,000 |
| 83 | $-N(CH_3)CH_2CH_2CH_2N(CH_3)_2$ | 1,797,000 |
| 84 | $-NHCH_2CH_2N(i\text{-}Pr)_2$ | 2,100,000 |
| 85 | $-N(CH_3)CH_2CH_2N(O)(CH_3)_2$ | 1,589,000 |
| 86 | $-N(CH_3)CH_2CH_2N(i\text{-}Pr)_2$ | 2,449,000 |
| 87 | $-NH-SO_2CH_2CH_2$-(4-morpholinyl) | 775,000 |
| 88 | $-NH-SO_2CH_2CH_2N(CH_3)_2$ | 788,000 |
| 89 | $-NHCH_2CH_2$-(4-imidazolyl) | 2,092,000 |
| 90 | $-NHCH_2CH_2$-(1-piperidinyl) | 941,000 |
| 91 | $-N(CH_3)CH_2CH_2$-(1-piperidinyl) | 892,000 |
| 92 | $-N(CH_3)CH_2CH_2NHCH_3$ | 1,453,000 |
| 93 | $-N(CH_3)CH_2CH_2N(CH_3)Ac$ | 1,960,000 |
| 94 | $-NHCH_2CH_2$-(1-pyrrolidinyl) | 1,239,000 |
| 95 | $-N(CH_3)CH_2CH_2$-(1-pyrrolidinyl) | 1,005,000 |
| 96 | $-NHCH_2CH_2$-(1H-1,2,4-triazol-1-yl) | 1,397,000 |
| 97 | $-NH-CH_2CH_2$-(1-imidazolyl) | 1,070,000 |
| 98 | $-NH-CH_2CH_2$-(3-azabicyclo-[3.2.2-non-3-yl) | 3,043,000 |
| 99 | $-NH-CH_2CH_2$-(3-azaspiro[5.5]-undec-3-yl) | 2,583,000 |
| 100 | $-NH-CH_2CH_2$-(2H-tetrazol-2-yl) | 2,006,000 |
| 101 | $-NH-CH_2CH_2$-(1H-tetrazol-1-yl) | 2,053,000 |
| 102 | $-NHCH_2C(O)-Pro-NHCH_2Ph$ | 2,747,000 |
| 103 | $-N(CH_3)CH_2CH_2$-(3-azabicyclo-[3.2.2]non-3-yl) | 2,996,000 |
| 104 | $-N(CH_3)CH_2CH_2$-(4-imidazolyl) | 2,389,000 |
| 105 | $-N(CH_3)CH_2CH_2N(CH_3)Ac$ | 2,398,000 |
| 106 | $-N(CH_3)CH_2CH_2N(CH_3)C(O)NHCH_3$ | 2,486,000 |
| 107 | $-N(CH_3)CH_2CH_2N(CH_3)SO_2CH_3$ | 2,530,000 |
| 108 | $-N(CH_3)CH_2CH_2$(3-azabicyclo-[3.2.2]-non-3-yl) | 2,953,000 |
| 109 | $-NHCH_2CH_2$-(1,1-dioxo-4-thiamorpholinyl) | 1,275,000 |
| 110 | 4-dimethylaminobenzylamino | 5,598,000 |
| 111 | 3-dimethylaminoanilino | 2,286,000 |
| 112 | $-N(CH_3)CH_2CH_2$-(1,1-dioxo-4-thia-morpholinyl) | 1,596,000 |
| 113 | 4-dimethylaminoanilino | 2,591,000 |
| 114 | $-NHCH_2CH_2$-(1-benzyl-1H-imidazol-2-yl) | 3,853,000 |
| 115 | $-N(CH_3)CH_2CH_2$(2-pyridyl) | 2,272,000 |
| 116 | $-N(CH_3)$(1-azabicyclo[2.2.2]oct-3-yl | 3,480,000 |
| 117 | $-NHCH_2CH_2$(4-benzyloxycarbonyl-1-piperazinyl) | 6,231,000 |
| 118 | 1,2-diethylpyrazolidin-4-ylamino | 1,001,000 |
| 119 | 2-(1-S-pyrrolidinylmethyl)-1-pyrrolidinyl | 2,692,000 |
| 120 | $-NHCH_2CH_2$(4-hydroxy-1-piperidinyl) | 1,728,000 |
| 121 | $-NHCH_2CH_2$(1-homopiperidinyl) | 2,069,000 |
| 122 | $-N(CH_3)CH_2CH_2$(1-homopiperidinyl) | 2,899,000 |
| 123 | $-NHCH_2CH_2$(3-hydroxy-1-piperidinyl) | 1,534,000 |
| 124 | $-N(CH_3)CH_2CH_2$(3-hydroxy-1-piperidinyl) | 1,963,000 |
| 125 | $-N(CH_3)CH_2CH_2N(CH_3)CH_2Ph$ | 2,054,000 |
| 126 | $-N(CH_3)CH_2CH_2$(4-benzyloxy-1-piperidinyl) | 3,476,000 |
| 127 | $-N(n\text{-}Pr)_2$ | 990,000 |
| 128 | $-N(Et)_2$ | 1,454,000 |
| 129 | $-N(CH_3)CH_2CH_2$(4-hydroxy-1-piperidinyl) | 1,994,000 |
| 130 | $-N(CH_3)CH_2CH_2$(4-oxo-1-piperidinyl) | 2,297,000 |
| 131 | $-NHCH_2CH_2$(3-hydroxy-1-pyrrolidinyl) | 1,111,000 |
| 132 | $-N(Et)CH_2CH_2$(1-piperidinyl) | 1,244,000 |
| 133 | $-N(CH_2Ph)CH_2CH_2$(1-piperidinyl) | 1,521,000 |
| 134 | 4-fluoroanilino- | 724,000 |
| 135 | 3-chloroanilino- | 201,000 |
| 136 | 3-methoxyanilino | |

TABLE 4-continued

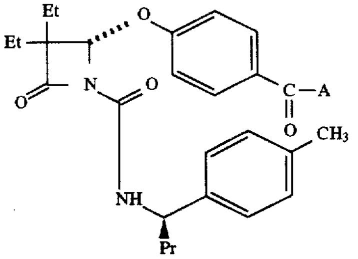

| No. | A | Kobs/[I] |
|---|---|---|
| 137 | $-N(CH_2Ph)CH_2CH_2N(CH_3)_2$ | 1,380,000 |
| 138 | $-N(CH_3)CH_2CH_2$(3-hydroxy-1-pyrrolidinyl) | 960,000 |
| 139 | $-N$(3-picolyl)$CH_2CH_2$(1-piperidinyl) | 1,189,000 |
| 140 | $-NHCH(CH_3)CH_2CH_2CH_2N(Et)_2$ | 1,361,000 |
| 141 | $-NHCH_2CH_2$(2-S-hydroxymethyl-1-pyrrolidinyl | 1,507,000 |
| 142 | $-N(CH_3)CH_2CH_2$(4-t-butoxycarbonyl-1-piperazinyl) | 3,471,000 |
| 143 | $-N[CH_2CH_2N(CH_3)_2]_2$ | 1,878,000 |
| 144 | $-N[CH_2CH_2N(Et)_2]_2$ | 1,508,000 |
| 145 | $-N(CH_3)CH_2CH_2N(CH_3)$(3-picolyl) | 2,877,000 |
| 146 | 3,5-dimethyl-1-piperazinyl | 1,518,000 |
| 147 | $-N(CH_3)CH_2CH_2N(O)(CH_3)CH_2Ph$ | 2,493,000 |
| 148 | $-N(CH_3)CH_2CH_2N(CH_3)$(4-picolyl) | 2,389,000 |
| 149 | 2-S-(N-benzyl-N-methylaminomethyl)-1-pyrrolidinyl | 3,268,000 |
| 150 | $-N(CH_3)CH_2CH_2N(CH_3)$(2-picolyl) | 2,165,000 |
| 151 | $-N(CH_3)CH_2CH_2$(1-piperazinyl) | 1,191,000 |
| 152 | 1-homopiperazinyl | 1,951,000 |
| 153 | $-N(CH_3)CH_2CH_2N(CH_3)CH_2CH_2Ph$ | 2,797,000 |
| 154 | 2-(1-R-pyrrolidinylmethyl)-1-pyrrolidinyl | 1,666,000 |
| 155 | 4-benzyl-1-homopiperazinyl | 1,979,000 |
| 156 | $-N(CH_3)CH_2-[CH(OH)]_4CH_2OH$ | 1,198,000 |
| 157 | $-N(CH_3)CH_2-[CH(OAc)]_4CH_2OAc$ | 1,171,000 |
| 158 | $-N(CH_3)CH_2CH_2N(CH_3)$(1-Naphthalenylmethyl) | 1,075,000 |
| 159 | $-N(CH_3)CH_2CH_2N(CH_3)$(2-Naphthalenylmethyl) | 1,337,000 |
| 160 | $-N(CH_3)CH_2CH_2N(CH_3)CH(CH_3)Ph$ | 1,569,000 |
| 161 | $-N(CH_3)CH_2CH_2N(CH_2Ph)_2$ | 1,021,000 |
| 162 | 1-ethyl-3-piperidinylamino | 949,000 |
| 163 | $-N(CH_3)CH_2CH_2N(CH_3)$(2-furfuryl) | 1,818,000 |
| 164 | $-N(CH_3)CH_2CH_2CH_2CO_2H$ | 1,064,000 |
| 165 | $-N(CH_3)CH_2CH_2CH_2C(O)NHSO_2Ph$ | 1,550,000 |
| 166 | $-N(CH_3)CH_2CH_2N(CH_3)CH_2CH{=}CH_2$ | 1,359,000 |
| 167 | $-N(CH_3)CH_2CH_2CH_2N(CH_3)CH_2Ph$ | 1,293,000 |
| 168 | $-N(CH_3)-(CH_2)_6-N(CH_3)CH_2Ph$ | 2,157,000 |
| 169 | $-N(CH_3)CH_2CH_2OH$ | 1,457,000 |
| 170 | $-N(CH_3)CH_2CH_2OC(O)N(CH_3)_2$ | 1,518,000 |
| 171 | $-N(CH_3)CH_2CH_2N(CH_3)CH_2CO_2$-t-Bu | 1,831,000 |
| 172 | $-N(CH_3)$(1-ethyl-3-piperidinyl) | 1,545,000 |
| 173 | $-N(CH_3)CH_2CH_2N(CH_3)$(tetrahydro-2H-pyran-2-yl-methyl) | 2,943,000 |
| 174 | 2,2,6,6-tetramethylpiperidin-4-ylamino | 869,000 |
| 175 | $-N(CH_3)$(4-carboxyphenyl) | 1,055,000 |
| 176 | $-N(CH_3)$(4-benzenesulfonylaminocarbonyl-phenyl | 3,231,000 |
| 177 | $-N(CH_3)CH_2CH_2N(CH_3)$(4-cyanobenzyl) | 2,201,000 |
| 178 | $-N(CH_3)CH_2CH_2N(CH_3)$(4-methylbenzyl) | 1,870,000 |
| 179 | $-N(CH_3)CH_2CH_2N(CH_3)$(3-cyanobenzyl) | 2,448,000 |
| 180 | $-N(CH_3)CH_2CH_2N(CH_3)$(4-trifluoro-methylbenzyl | 905,000 |
| 181 | $-N(CH_3)CH_2CH_2N(CH_3)$(3-trifluoromethyl-benzyl) | 564,000 |
| 182 | $-N(CH_3)CH_2CH_2(CH_3)$(4-fluorobenzyl) | 2,137,000 |
| 183 | $-NHCH(CH_3)PH(O)OH$ | 977,000 |
| 184 | L-lysine (α-N) | 755,000 |
| 185 | $-N(CH_3)CH_2CH_2N(CH_3)$(cyclopropylmethyl) | 1,787,000 |
| 186 | $-N(CH_3)CH_2CH(Ph)N(CH_3)_2$ | 1,053,000 |
| 187 | $-N(CH_3)_2$ | 1,749,000 |
| 188 | $-N(CH_3)CH_2Ph$ | 1,837,000 |
| 189 | $-N(CH_3)$(1-benzyl-3-piperidinyl) | 1,879,000 |
| 190 | $-NH-O-CH_2Ph$ | 1,797,000 |
| 191 | $-N$(3-picolyl)$CH_2CH_2N(CH_3)CH_2PH$ | 2,538,000 |
| 192 | $-N(CH_3)CH_2CH_2N(CH_3)$(4-methoxybenzyl) | 1,785,000 |
| 193 | $-N$(4-picolyl)$CH_2CH_2N(CH_3)CH_2Ph$ | 2,243,000 |
| 194 | $-N$(2-picolyl)$CH_2CH_2N(CH_3)CH_2Ph$ | 2,473,000 |
| 195 | $-N(CH_3)CH_2CH_2N(CH_3)$(2,4-dimethylbenzyl) | 1,119,000 |
| 196 | $-N(CH_3)CH_2CH_2$(2,6-dimethyl-4-morpholinyl) | 1,530,000 |
| 197 | $-NH_2$ | 1,638,000 |
| 198 | $-NHCH_3$ | 1,825,000 |
| 199 | 4-morpholinyl | 2,376,000 |
| 200 | cis-2,6-dimethyl-4-morpholinyl | 1,837,000 |

TABLE 4-continued

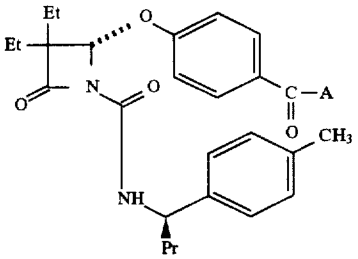

| No. | A | Kobs/[I] |
|---|---|---|
| 201 | $-NH-CH_2CH_2CH_2CH_3$ | 2,460,000 |
| 202 | $-N(CH_3)CH_2CH_2N(CH_3)C(=N-CN)NHPh$ | 1,763,000 |
| 203 | $-N(CH_3)CH_2CH_2N(CH_3)$(3-fluorobenzyl) | 1,262,000 |
| 204 | $-N(CH_3)CH_2CH_2N(CH_3)$(2-chlorobenzyl) | 1,591,000 |
| 205 | $-N(CH_3)CH_2CH_2N(CH_3)$(3-methoxybenzyl) | 1,911,000 |
| 206 | $-N(CH_3)CH_2CH_2N(CH_3)$(3,5-dimethoxybenzyl) | 1,735,000 |
| 207 | 3,4-dihydro-6,7-dimethoxy-2-(1H)iso-quinolinyl | 2,698,000 |
| 208 | $-N(CH_3)$(1-benzyl-4-piperidinyl) | 1,948,000 |
| 209 | L-lysine (ε-N) | 929,000 |
| 210 | $-N(CH_3)CH_2CH_2N(CH_3)$(2-adamantyl) | 2,132,000 |
| 211 | $-N(CH_3)$(4-piperidinyl) | 85,000 |
| 212 | 5-Methyl-2,5-diazabicyclo[2.2.1]hept-2-yl | 860,000 |
| 213 | $-N(CH_3)CH_2CO_2H$ | 984,000 |
| 214 | $-N(CH_3)CH_2CH_2CH_2N(CH_3)CH_2CH_3$ | 1,099,000 |
| 215 | $-N(CH_3)$(1-methyl-4-piperidinyl) | 1,283,000 |
| 216 | $-N(CH_3)$(1-propyl-4-piperidinyl) | 1,312,000 |
| 217 | $-N(CH_3)$(1-ethyl-4-piperidinyl) | 1,422,000 |
| 218 | $-N(CH_3)CH_2CH(CH_3)N(CH_3)CH_2Ph$ | 2,123,000 |
| 219 | $-N(CH_3)CH_2CH(CH_3)N(CH_3)_2$ | 1,588,000 |
| 220 | $-N(CH_3)CH_2CH_2N(CH_3)$(bicyclo[2.2.1]-hept-2-yl) | 1,874,000 |
| 221 | $-N(CH_3)CH_2CH_2NH$(2-adamantyl) | 3,010,000 |
| 222 | $-N(CH_3)CH_2CH_2N(CH_3)$(6,6-dimethylbicyclo-[3.1.1]hept-2-yl | 2,288,000 |
| 223 | $-N(CH_3)CH_2CH_2N(CH_3)$(bicyclo[3.2.1]-oct-2-yl) | 2,584,000 |
| 224 | $-NH$(t-Bu) | |
| 225 | $-N(CH_3)CH_2CH_2N(CH_3)$(1-cyclohexen-1-yl) | 1,839,000 |
| 226 | $-N(CH_3)CH_2CH_2NHC(CH_3)_2CH=CH_2$ | 1,309,000 |
| 227 | 2-S-carboxamido-1-pyrrolidinyl | 931,000 |
| 228 | 2-hydroxymethyl-1-piperidinyl | 50,000 |
| 229 | 3-dimethylamino-1-pyrrolidinyl | 1,336,000 |
| 230 | $-N(CH_3)CH_2CH_2N(CH_3)$(cyclohexylmethyl) | |
| 231 | $-N(CH_3)CH_2CH_2N(CH_2CH=CH_2)C(CH_3)_2CH=CH_2$ | 925,000 |
| 232 | $-N(CH_3)CH_2CH_2N(CH_3)$(4-ethylcyclohexyl) | 2,476,000 |
| 233 | $-N(CH_3)CH_2CH_2N(CH_3)$(2-ethylcyclohexyl) | 2,030,000 |
| 234 | $-N(CH_3)CH_2CH_2N(CH_3)$(4-methylcyclohexyl) | 2,166,000 |
| 235 | $-N(CH_3)CH_2CH_2N(CH_3)$(cyclohexyl) | 1,952,000 |
| 236 | $-N(CH_3)CH_2CH_2N(CH_3)CH_2CO_2H$·TFA | 31,000 |
| 237 | $-N(CH_3)CH_2CH_2N(CH_3)CH_2C(O)N(CH_3)_2$ | 2,679,000 |
| 238 | 3-dimethylamino-1-azetidinyl | |
| 239 | 1-diphenylmethyl-3-azetidinyl | |
| 240 | $-N(CH)CH_2CH_2N(CH_3)$(cyclohexylmethyl) | 3,003,000 |
| 241 | $-NHCH_2CH_2N(Et)CH_2CH_2OCH_3$ | 1,090,000 |

TABLE 5

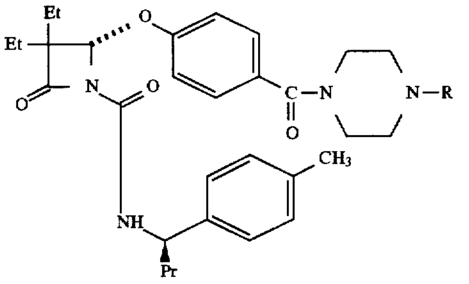

| No. | R | Kobs/[I] |
|---|---|---|
| 242 | $-CH3$ | 1,700,000 |
| 243 | 4-fluorophenyl | 7,486,000 |
| 244 | 3-chlorophenyl | 2,453,000 |
| 245 | phenyl | 5,276,000 |
| 246 | benzyl | 5,171,000 |
| 247 | H | 1,100,000 |
| 248 | i-Pr | 2,392,000 |
| 249 | i-Bu | 2,476,000 |
| 250 | $-CH_2CO_2Et$ | 1,571,000 |
| 251 | $-CH_2CO_2H$ | 1,947,000 |
| 252 | Et | 2,324,000 |
| 253 | Pr | 1,768,000 |
| 254 | 2-pyrimidinyl | 2,142,000 |
| 255 | $-CH_2CH_2OC(O)NHCH_3$ | 2,548,000 |
| 256 | cyclopropyl | 3,587,000 |
| 256a | $-CH_2CH_2OH$ | 2,000,000 |

TABLE 6

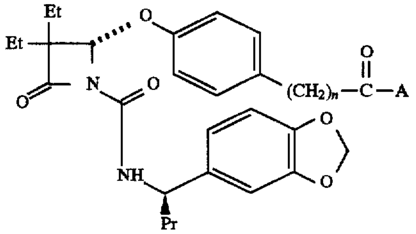

| No. | n | A | Kobs/[I] |
|---|---|---|---|
| 257 | 1 | $NH_2$ | 2,342,000 |
| 258 | 1 | 4-morpholinyl | 1,785,000 |
| 259 | 1 | $-N(CH_3)CH_2CH_2N(CH_3)_2$ | 2,522,000 |
| 260 | 0 | $-N(CH_3)CH_2CH_2N(CH_3)_2$ | 3,317,000 |
| 261 | 0 | $-N(Et)_2$ | 3,207,000 |
| 262 | 0 | $-N(CH_3)(n\text{-}Bu)$ | 3,125,000 |
| 263 | 0 | 4-methyl-1-piperazinyl | 3,805,000 |
| 264 | 0 | $-N(CH_3)CH_2CH_2N(CH_3)CH_2Ph$ | 3,427,000 |
| 265 | 0 | 4-cyclopropyl-1-piperazinyl | 4,500,000 |
| 265a | 0 | 1-piperazinyl | 3,250,000 |
| 265c | 0 | 4-(2-hydroxyethyl)-1-piperazinyl | 4,800,000 |
| 265d | 0 | 4-morpholinyl | 3,700,000 |

TABLE 7

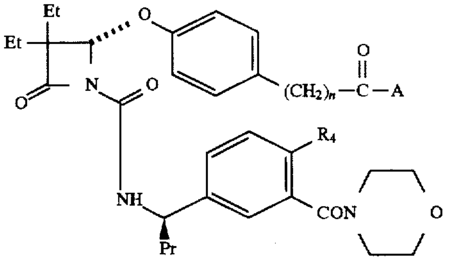

| No. | n | $R_4$ | A | Kobs/[I] |
|---|---|---|---|---|
| 266 | 1 | H | 4-morpholinyl | 169,000 |
| 267 | 1 | H | $-N(Et)_2$ | 334,000 |
| 268 | 1 | H | $-N(CH_3)CH_2CH_2N(CH_3)_2$ | 142,000 |
| 269 | 1 | $CH_3$ | $NH_2$ | 637,000 |
| 270 | 1 | $CH_3$ | $N(Et)_2$ | 740,000 |
| 271 | 1 | $CH_3$ | $N(n\text{-}Pr)_2$ | 826,000 |
| 272 | 0 | Et | $-N(CH_3)CH_2CH_2N(CH_3)_2$ | 2,423,000 |
| 273 | 0 | Et | $-N(CH_3)(n\text{-}Bu)$ | 3,258,000 |

TABLE 8

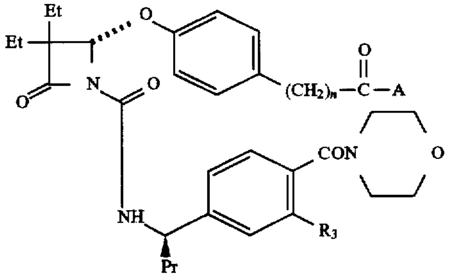

| No. | n | $R_3$ | A | Kobs/[I] |
|---|---|---|---|---|
| 274 | 1 | H | $NH_2$ | 430,000 |
| 275 | 1 | H | $-N(CH_3)CH_2CH_2N(CH_3)_2$ | 290,000 |
| 276 | 1 | H | $-OCH_3$ | 440,000 |
| 277 | 0 | H | $-N(CH_3)CH_2CH_2N(CH_3)_2$ | 548,000 |
| 278 | 0 | H | $-OCH_2CH_2N(CH_3)_2$ | 135,000 |
| 279 | 0 | H | $-N(Et)_2$ | 566,000 |
| 280 | 0 | H | 4-morpholinyl | 577,000 |

TABLE 9

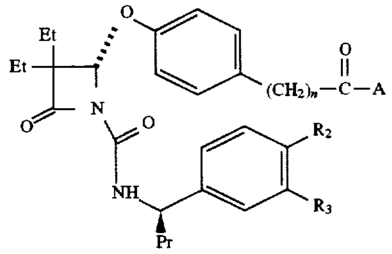

| No. | n | $R_3$ | $R_2$ | A | Kobs/[I] |
|---|---|---|---|---|---|
| 281 | 1 | H | $CO_2H$ | 4-morpholinyl | 62,000 |
| 282 | 1 | H | $-CO_2CH_2CH_2N(CH_3)_2$ | 4-morpholinyl | 421,000 |
| 283 | 1 | H | $-CON(CH_3)CH_2CH_2N(CH_3)_2$ | 4-morpholinyl | 393,000 |
| 284 | 1 | H | $-OH$ | $-N(CH_3)CH_2CH_2N(CH_3)_2$ | 309,000 |
| 285 | 1 | H | $OCH_3$ | $-N(CH_3)CH_2CH_2N(CH_3)_2$ | 566,000 |
| 286 | 0 | H | $-CON(CH_3)_2$ | $-N(CH_3)CH_2CH_2N(CH_3)_2$ | 551,000 |
| 287 | 0 | H | $-CO_2H$ | $-N(CH_3)CH_2CH_2N(CH_3)_2$ | 113,000 |
| 288 | 0 | H | $-CH_2OH$ | $-N(CH_3)CH_2CH_2N(CH_3)_2$ | 854,000 |
| 289 | 1 | H | $OCH_3$ | $-N(CH_3)CH_2CH_2N(CH_3)_2$ | 754,000 |
| 290 | 0 | H | $OCH_3$ | $-N(CH_3)CH_2CH_2N(CH_3)_2$ | 1,010,000 |
| 291 | 0 | $OCH_3$ | H | $-N(CH_3)CH_2CH_2N(CH_3)_2$ | 1,754,000 |
| 292 | 1 | $-CH_2OCON(Et)_2$ | $CH_3$ | 4-morpholinyl | 807,000 |
| 293 | 1 | $-CON(n-Pr)_2$ | $CH_3$ | $-N(Et)_2$ | 457,000 |
| 294 | 1 | $CON(n-Pr)_2$ | $CH_3$ | 4-morpholinyl | 255,000 |
| 295 | 0 | H | CN | $-N(CH_3)CH_2CH_2N(CH_3)_2$ | 846,000 |
| 296 | 0 | H | OEt | $-N(CH_3)CH_2CH_2N(CH_3)CH_2Ph$ | 776,000 |
| 297 | 0 | H | 2-(4-morpholinocarbonylphenyl) | $-N(CH_3)CH_2CH_2N(CH_3)CH_2Ph$ | 1,077,000 |
| 298 | 0 | H | $OCH_3$ | 4-methyl-1-piperazinyl | 1,845,000 |
| 299 | 0 | H | Cl | $-N(CH_3)CH_2CH_2N(CH_3)_2$ | 1,475,000 |
| 300 | 0 | H | Cl | $-N(CH_3)CH_2CH_2N(Et)_2$ | 1,282,000 |
| 301 | 0 | H | Cl | $-N(CH_3)CH_2CH_2N(i-Pr)_2$ | 1,497,000 |
| 302 | 0 | H | Cl | $-N(CH_3)CH_2CH_2N(CH_3)CH_2Ph$ | 1,462,000 |
| 303 | 0 | $OCH_3$ | $CH_3$ | $-N(CH_3)CH_2CH_2N(CH_3)_2$ | |

TABLE 10

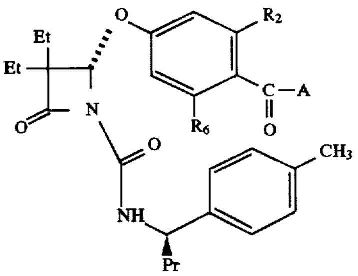

| No. | $R_2$ | $R_6$ | A | Kobs/[I] |
|---|---|---|---|---|
| 304 | $CH_3$ | $CH_3$ | $-OCH_2CH_2N(CH_3)_2$ | 563,000 |
| 305 | $CH_3$ | $CH_3$ | $-OCH_2CH_2N(Et)_2$ | 749,000 |
| 306 | $CH_3$ | $CH_3$ | $-OCH_2CH_2N(i-Pr)_2$ | 612,000 |
| 307 | $CH_3$ | $CH_3$ | $-N(CH_3)CH_2CH_2N(CH_3)_2$ | 352,000 |
| 308 | $CH_3$ | $CH_3$ | $-N(CH_3)CH_2CH_2N(Et)_2$ | 377,000 |
| 309 | $CH_3$ | $CH_3$ | $-N(Et)CH_2CH_2N(CH_3)_2$ | 398,000 |
| 310 | H | OH | $-N(CH_3)CH_2CH_2N(CH_3)_2$ | 838,000 |

Enzyme Assays for the Inhibition of Human Polymorphonuclear Leukocyte Elastase Via Hydrolysis of N-t-Boc-alanyl-alanyl-prolylalanine-p-nitroanilide (Boc-AAPAN) or N-t-Boc-alanyl-prolylvaline-p-nitroanilide (Boc-AAPVN) Reagent:

0.05M TES (N-tris[hydroxymethyl]methyl-2-mino-ethanesulfonic acid) Buffer, pH 7.5.

0.2mM Boc-AAPAN or Boc-AAPVN.

To prepare substrate, the solid was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidinones) to be tested dissolved in DMSO just before use.

To 1.0 ml of 0.2 mM Boc-AAPAN in a cuvette, 0.01–0.1 ml of DMSO with or without inhibitor was added. After mixing, a measurement was taken at 410 mμ to detect any spontaneous hydrolysis due to presence of test compound. 0.05 Milliliters of PMN extract was then added and the ΔOD/min at 410 mμ was measured and recorded. Beckman model 35 spectrophotometer was used.

Results were expressed to the nearest thousand $^k$obs/I which is the second order rate constant in per mole per second for inactivation of the enzyme.

The elastase activity in the crude PMN extract may vary from one preparation to another. A control of each new batch is run, and the volume added in the assay procedure is adjusted according to activity.

This invention also relates to a method of treating inflammation in patients using a compound of Formula (I), particularly a preferred compound as the active constituent.

It has been found that the compounds of Formula (I) are effective inhibitors of the proteolytic function of human neutrophil elastase.

Accordingly, the compounds of Formula (I), can be used to reduce inflammation and/or relieve pain in diseases such as emphysema, rheumatoid arthritis, osteoarthritis, gout, bronchial inflammation, chronic or acute bronchitis, cystic fibrosis, adult respiratory distress syndrome, atherosclerosis, sepsis, septicemia, shock, periodontitis, glomerular nephritis or nephosis, myocardial infarction, reperfusion injury, infectious arthritis, rheumatic fever and the like, and may reduce hemorrhage in acute promyelocytic leukemia and the like.

In this capacity, and as appreciated by those of skill in the art, therapy comprising administration of compounds of Formula I may actually include co-administration of one or more additional active agents. Classes of active agents include, but are not limited to $\beta_2$-adrenergic agonists; anti-cholinergic agents; steroids; non-steroidal anti-inflammatory agents (NSAID's); mucolytic agents; most all stabilizers; and antibacterials.

For purposes of this specification, $\beta_2$-adrenergic agonists are intended to include, but are not limited to, metaproterenol, terbutaline, isoetharine, albuterol, and ritodrine, carbuterol, fenoterol, quinterenol, rimiterol, salmefamol, soterenol, and tretoquinol.

For purposes of this specification, anti-cholinergic agents are intended to include, but are not limited to, atropine, and iptratropium-bromide.

For purposes of this specification, mucolytic agents are intened to include, but are not limited to acetylcysteine and guattenesin.

For purposes of this specification, steroids are intended to include, but are not limited to, prednisone, beclomethasone, budesonide, solumedrol, triamcinolone, and methyl-prednisolone.

For purposes of this specification most cell stabilizers are intended to include, but are not limited to cromolyn and ketotafin.

For purposes of this specification, non-steroidal anti-inflammatory agents are intended to include, but are not limited to aspirin, diflunisal, naphthylsalicylate, phenylbutazolone, oxyphenbutazolone, indomethacin, sulindac, mefenamic acid, meclofenamate sodium, tolmetin, ibuprofen, naproxen, fenoprofen and piroxicam.

For the purposes of this specification, antibacterial agents are intended to include the broad classes of penicillins, cephalosporins and other beta-lactams, aminoglycosides, quinolones, macrolides, tetracyclines, sulfonamides, lincosamides and polymyxins. The penicillins, in turn, are intended to include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams are intended to include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxome, ceftizoxime, cetriaxone, cephoperazone, ceftazidime, imipenem and aztreonam. The aminoglycosides are intended to include, but are not limited to streptomycin, gentamicin, tobramycin, amikacin, netilmicin, kanamycin and neomycin. The quinolones are intended to include, but are not limited to nalidixic acid, norfloxacin, enoxacin, ciprofloxacin, ofloxacin, sparfloxacin and temafloxacin. The macrolides are intended to include, but are not limited to erythomycin, spiramycin and azithromycin. The tetracyclines are intended to include, but are not limited to doxycycline, minocycline and tetracycline. The sulfonamides are intended to include, but are not limited to sulfanilamide, sulfamethoxazole, sulfacetamide, sulfadiazine, sulfisoxazole and co-trimoxazole (trimethoprim/sulfamethoxazole). The lincosamides are intended to include, but are not limited to clindamycin and lincomycin. The polymyxins (polypeptides) are intended to include, but are not limited to polymyxin B and colistin.

Alternatively, compounds of Formula I are useful in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocyte leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation.

Similarly, compounds of Formula I are useful for the inhibition of proteinase 3/myeloblastin, inhibition of elastase, inhibition of proliferation of leukemia cells, inducing differentiation of leukemia cells and remission of the disease state of leukemia.

Moreover, as described above, such treatment may optionally comprise the co-administration of an agent such as a compound selected from the group consisting of epsilon-aminocaproic acid, heparin, trasylol, prednisolone, cytosine arabinoside, b-mercaptopurine, cytarabine, an anthracycline and a vitamin A derivative such as retinoic acid.

For each of the uses, the compounds of Formula (I) and optional treatment agents, may be administered orally, topically, parenterally, by inhalation spray or rectally in dosage unit Formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

For treatment as described above the compounds of Formula (I) may be administered orally, topically, parenterally, by inhalation spray or rectally in dosage unit Formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives.

Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution glucose in water and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The amount of active ingredient(s) that may be combined with the carrier materials to produce a single dosage form will vary depending upon the host treated and the particular mode of administration.

For example, a formulation intended for the oral administration of humans may contain from 5 mg to 2000 mg or 5000 mg of each active agent(s) compounded with an appropriate and convenient amount of carrier material which may vary from about 5 to about 95 percent of the total composition. For purposes of this specification, this broad dosage range is specifically intended to include, but is not limited to, range of 5 mg to 2000 mg; 25 mg to 2000 mg; 5 mg to 1000 mg; 25 mg to 1000 mg; 5 mg to 500 mg; and 25 mg to 500 mg. Dosage unit forms will generally contain between from about 25 mg to about 500 mg of active ingredient(s).

Furthermore, it is also possible that most effective treatment may warrent administration of an initial dosage of one range (e.g. 1–5 mg of active agent per kg of patient weight) followed by administration of a second range (e.g. 0.1 to 1 mg of active agent per kg of pateint weight).

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following example illustrates the preparation of the compounds useful in the method of treatment of the present invention, but does not limit the scope of the invention. Starting materials may be optionally prepared as disclosed in EPO 337 549 published Oct. 18, 1989 which is hereby incorporated by reference. Where appropriate, compounds may be produced and used in the form of pharmaceutically acceptable salts. For example, the basic coumpounds may be used in the form of a hydrochloride or mesylate or other acceptable salt.

See Preformulation in Remington's Pharmaceutical Sciences, Mack Publishing, Easton Pa.

SCHEME 1
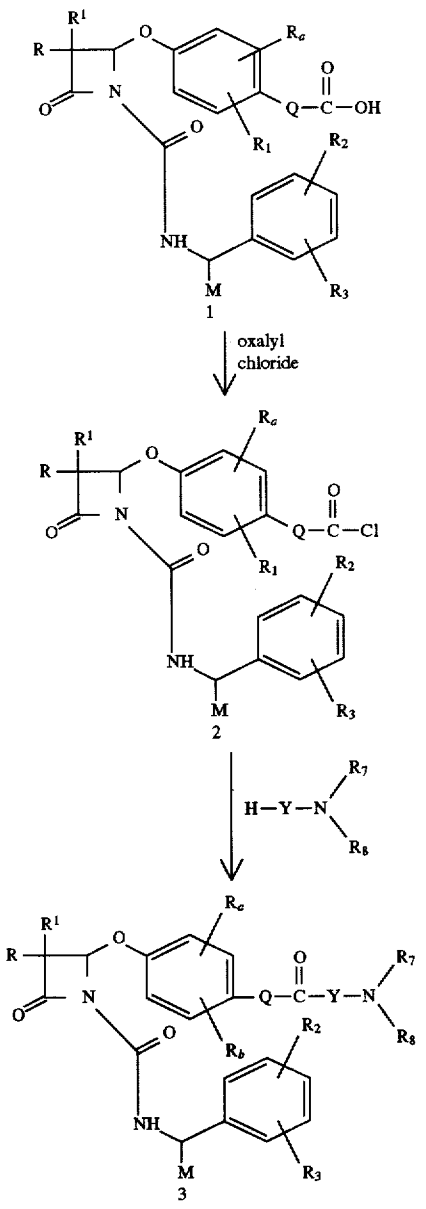
SCHEME 2
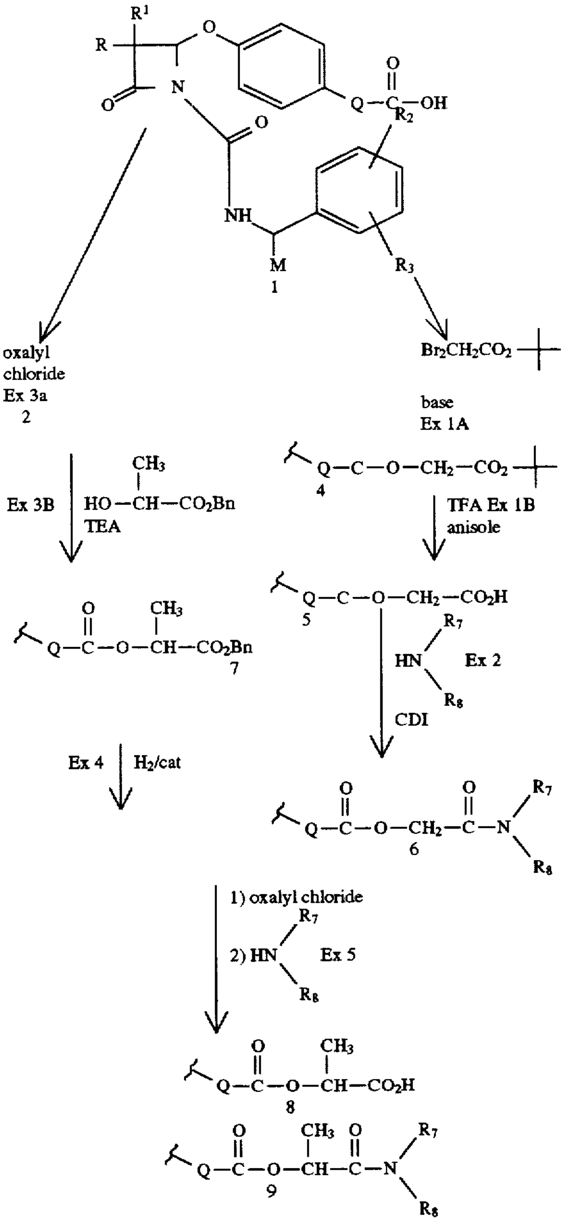

The glycolic acid derivatives described herein can be prepared according to the following scheme. The starting acid (as carboxylate anion) may be alkylated (Ex 1A) with a suitably protected α-halo acetic acid derivative to give the glycolate ester 4 which can be deprotected (Ex 1B) to the glycolic acid ester 5. Treatment of 5 with an amine utilizing a condensing agent such as dicyclohexylcarbodiimide or carbomyldiinidazole (Ex 2) affords the deserved amide 6. Alternately, the starting acid 1 may be converted to its acid chloride 2 (Ex 3A) and treated with a suitably protected α-hydroxyalkanoic acid (Ex 3B) in the presence of base to give the protected ester 7. Deprotection (Ex 4), followed by conversion to the acid chloride and treatment with the appropriate amine (Ex 5) affords the desired amide 9.

EXAMPLE 1

A. t-Butoxycarbonylmethyl [S-(R*, S*)]4-((3,3-diethyl-1-(((1-(4-methylphenyl)butyl)amino)-carbonyl)-4-oxo-2-azetidinyl)oxy)benzoate.

To a solution of 0.806 gm of [S-(R*, S*)]4-((3,3-diethyl-1-(((1-(4-methylphenyl)butyl)amino)-carbonyl)-4-oxo-2-azetidinyl)oxy)benzoic acid in ~3 ml DMF is added 0.23 gm. triethylamine followed by 0.50 gm of t-butyl bromoacetate and the mixture stirred overnight at room temperature. Ethyl acetate (25 ml) is then added and the resultant mixture is washed with 2–10 ml water, 10 ml saturated sodium bicarbonate, and 20 ml brine. The organic layer is dried through sodium sulfate and concentrated in vacuo. Chromatography on Silica gel 60 (350 ml column) and elution with 10% ethyl acetate in hexanes gave 0.67 gm of the t-Butoxycarbonylmethyl [S-(R*, S*)]4-((3,3-diethyl-1-(((1-(4-methyl-phenyl)butyl)amino)carbonyl)-4-oxo-2-azetidinyl)oxy) benzoate.

In a similar manner can be prepared 2-(dimethylamino)-2-oxoethyl, (S-(R*,S*))-4-((3,3-Diethyl-1-(((1-(4-methylphenyl)butyl)amino) carbonyl)-4-oxo-2-azetidinyl)oxy)-benzoate (Compound 6), and 2-(N-methylacetamido)ethyl, {2-(R*,S*)}-4-{{3,3-Diethyl-1-{{{1-(4-methyl-phenyl) butyl}amino}carbonyl}-4-oxo-2-azetidinyl}oxy}-benzoate, (Compound 7).

B. Carboxymethyl [S-(R*,S*)]4-((3,3-diethyl-1-(((1-(4-methyl-phenyl)butyl)amino)carbonyl)- 4-oxo-2-azetidinyl)oxy)benzoate To the above ester is added 2 ml of anisole and the resulting mixture is cooled in an ice bath and 5 ml of ice cold trifluoroacetic acid is added. The reaction mixture is stirred cold for three hours then allowed to come to room temperature. After 30 minutes, the reaction mixture is concentrated in vacuo and the residue chromatographed on silica gel 60. Elution with 20% ethyl acetate in hexanes containing 1% acetic acid gives 0.53 gm of desired carboxymethyl [S-(R*, S*)]4-((3,3-diethyl-1-(((1-(4-methyl-phenyl)butyl)amino) carbonyl)-4-oxo-2-azetidinyl)oxy)benzoate.

Compound 2

| | | | |
|---|---|---|---|
| Analysis: | $C_{28}H_{34}N_2O_7$+0.3$H_2O$ | | |
| Calc: | C, 65.19; | H, 6.75; | N, 5.43 |
| Found: | C, 65.30; | H, 6.76; | N, 5.23 |

Compound 6

| | | | |
|---|---|---|---|
| Analysis: | $C_{30}H_{39}N_3O_6$+0.5$H_2O$ | | |
| Calc: | C, 65.91; | H, 7.38; | N, 7.60 |
| Found: | C, 65.71; | H, 7.63; | N, 7.50. |

Compound 7

| | | | |
|---|---|---|---|
| Analysis: | $C_{31}H_{41}N_3O_6$+0.6EtOAc | | |
| Calc: | C, 66.35; | H, 7.64; | N, 6.95 |
| Found: | C, 66.52; | H, 7.89; | N, 6.83. |

EXAMPLE 2

2-(bis(2-hydroxyethyl)amino)-2-oxoethyl(S-(R*,S*))-4-((3,3-diethyl-1-(((1-(4-methyl-phenyl)butyl)amino)-carbonyl)-4-oxo-2-azetidinyl)oxy) benzoate.

To a solution of 0.125 gm of the acid from 1B in 2–3 ml of methylene chloride is added 0.050 gm of carbonyldiimidazole. The mixture is stirred for 30 minutes at room temperature at which time 0.060 gm of diethanolamine is added along with 1 ml of DMF and 2 ml of methylene chloride. The resulting mixture is stirred overnight at room temperature then concentrated in vacuo. Silica gel chromatography of the residue using 2.5 to 5.0% methanol in methylene chloride gives 0.123 gm of the desired Compound 3, 2-(bis(2-hydroxyethyl)amino)-2-oxoethyl(S-(R*, S*))-4-((3,3-diethyl-1-(((1-(4-methyl-phenyl)butyl)amino)-carbonyl)-4-oxo-2-azetidinyl)oxy) benzoate.

Compound 3

| | | | |
|---|---|---|---|
| Analysis: | $C_{32}H_{43}N_3O_8$, +0.4$H_2O$ | | |
| Calc: | C, 63.53; | H, 7.30; | N, 6.95 |
| Found: | C, 63,51; | H, 7.45; | N, 6.95. |

Similarly were prepared

Compound 4

| | | | |
|---|---|---|---|
| Analysis: | $C_{31}H_{40}N_4O_7$ | | |
| Calc: | C, 64.12; | H, 6.94; | N, 9.65 |
| Found: | C, 64.12; | H, 7.18; | N, 9.44 |

Compound 5

| | | | |
|---|---|---|---|
| Analysis: | $C_{32}H_{43}N_3O_9$ +0.3$H_2O$ | | |
| Calc: | C, 62.08; | H, 7.09; | N, 6.79 |
| Found: | C, 61.89; | H, 7.39; | N, 6.88. |

Compound 8

| | | | |
|---|---|---|---|
| Analysis: | $C_{40}H_{47}N_3O_8$ | | |
| Calc: | C, 68.85; | H, 6.79; | N, 6.02 |
| Found: | C, 68.79; | H, 7.06, | N, 5.88. |

EXAMPLE 3—PREPARATION OF

1-Methyl-2-oxo-2-(phenylmethoxy)ethyl(2S-(1(S*), R*,-(R)))-4-((3,3-diethyl-1-(((1-(4-methylphenyl) butyl)-amino)carbonyl)-4-oxo-2-azetidinyl)oxy) benzoate, Compound 10.

A.

To a solution of 1.0 gm [S-(R*, S*)]4-((3,3-diethyl-1-((1-(4-methylphenyl)butyl)amino)carbonyl)-4-oxo-2-azetidinyl)oxy)benzoic acid in 10 ml methylene chloride is added 2 ml of oxalyl chloride followed by a catalytic amount of DMF. The reaction is stirred 1 hour at room temperature then concentrated in vacuo to yield the acid chloride which is used as is in the next step.

B.

A solution of the above acid chloride in 10 ml of methylene chloride is cooled in an ice bath and a solution of 1.25 gm benzyl L-lactate and 2.0 gm of triethylamine in 10 ml of methylene chloride is added. The mixture is stirred at room temperature overnight then concentrated in vacuo. Chromatography of the residue on silica gel using methylene chloride as the eluent yields 0.795 of the desired 1-Methyl-2-oxo-2-(phenylmethoxy)ethyl (2S-(1(S*),R*, (R)))-4-((3,3-diethyl-1-(((1-(4-methyl-phenyl)butyl)amino)carbonyl)-4-oxo-2-azetidinyl)oxy) benzoate, Compound 10.

| | | | |
|---|---|---|---|
| Analysis: | $C_{36}H_{42}N_2O_7$ | | |
| Calc: | C, 70.34; | H, 6.89; | N, 4.56. |
| Found: | C, 70.45; | H, 7.05; | N, 4.48. |

EXAMPLE 4 PREPARATION OF 1-carboxyethyl [S-(R*,S*)]4-((3,3-diethyl-1-(((1-(4-methyl-phenyl)butyl)amino)carbonyl)-4-oxo-2-azetidinyl)oxy)benzoate A mixture of 0.69 gm of the benzylester prepared in Example 3 and 0.2 gm 10% Pd/C in 10 ml of EtOAc is treated with hydrogen at 40 psi. When the reaction is complete the mixture is filtered and concentrated in vacuo to yield 0.56 gm of 1-carboxy-ethyl [S-(R*,S*)]4-((3,3-diethyl-1-(((1-(4-methylphenyl)butyl)amino)carbonyl)-4-oxo-2-azetidinyl)oxy)benzoate, Compound 11.

| | | | |
|---|---|---|---|
| Analysis: | $C_{29}H_{36}N_2O_7$ | | |
| Calc: | C, 66.40; | H, 6.92; | N, 5.34. |
| Found: | C, 66.66; | H, 7.26; | N, 5.05. |

EXAMPLE 5

2-(diethylamino)-1-methyl-2-ozoethyl[S-(R*,S*)]-4-((3,3-diethyl-1-(((1-(4-methyl-phenyl)butyl)amino)-carbonyl)-4-oxo-2-azetidinyl)oxy) benzoate The acid (0.250 gm) from Example 4 is treated with oxalyl chloride according to the procedure of Example 3A and the corresponding acid chloride is obtained. This material is dissolved in 5 ml methylene chloride and 0.4 ml of diethylamine added. After 1 hour the reaction mixture is concentrated in vacuo and the residue taken in ethyl acetate and washed with saturated sodium bicarbonate solution. The organic layer is dried through sodium sulfate, concentrated and the residue chromatographed on silica gel. Elution with 5% of ethyl acetate in methylene chloride gives Compound 12.

| | | | |
|---|---|---|---|
| Analysis: | $C_{33}H_{45}N_3O_6$ | | |
| Calc: | C, 68.37; | H, 7.82, | N, 7.25 |
| Found: | C, 68.40; | H, 7.93, | N, 7.40. |

EXAMPLE 6

(S(R*,S*))-1-(((4-((3,3-diethyl-1-(((1-(4-methyl-phenyl)butyl)amino)carbonyl)-4-oxo-2-azetidinyl)oxy)benzoyl)oxy)acetyl) L-proline,

A.

When benzyl L-lactate is replaced by L-proline benzyl ester hydrochloride and triethylamine in the procedure of Example 3 the corresponding amide with L-proline benzyl ester, Compound 8, is obtained.

| | | | |
|---|---|---|---|
| Analysis: | $C_{40}H_{47}N_3O_8$ | | |
| Calc: | C, 68.85; | H, 6.79, | N, 6.02 |
| Found: | C, 68.79; | H, 7.06, | N, 5.88. |

B.

Reduction of the material obtained in Example 6A according to the procedure of Example 4 affords Compound 9.

| | | | |
|---|---|---|---|
| Analysis: | $C_{33}H_{41}N_3O_8$+0.5$H_2O$ | | |
| Calc: | C, 64.27; | H, 6.86; | N, 6.81. |
| Found: | C, 64.49; | H, 6.90; | N, 6.68. |

EXAMPLE 7

[S-(R*,S*)]1-(((4-((3,3-diethyl-1-(((1-(4-methyl-phenyl)butyl)amino) carbonyl-4-oxo-2-azetidinyl) oxy)benzoyl)oxy)acetyl-N-benzyl-L-prolinamide.

Treatment of the acid obtained in Example 6B, Compound 9, with oxalyl chloride according to Example 3A gives the corresponding acid chloride which when treated with benzylamine gives the desired benzyl amide, Compound 19.

| | | | |
|---|---|---|---|
| Analysis: | $C_{40}H_{48}N_4O_7$ | | |
| Calc: | C, 68.95; | H, 6.94; | N, 8.04. |
| Found: | C, 68.93, | H, 7.02; | N, 7.96. |

EXAMPLE 8

To a solution of the acid chloride (prepared from 0.55 gm of [S-(R*,S*)]4-((3,3-diethyl-1-(((1-(4-methylphenyl)butyl)amino)carbonyl)-4-oxo-2-azetidinyl)oxy)benzoic acid according to the procedure of Example 3A) in 3 ml of methylene chloride is added 0.15 gm of N,N-dimethylaminoethanol. The reaction mixture is stirred overnight at room temperature, concentrated in vacuo, then taken up in ethyl acetate (25 ml) and washed with saturated sodium bicarbonate solution. The organic layer is dried through sodium sulfate and concentrated in vacuo. Silica gel chromatography of the residue using 2.5% methanol in methylene chloride gives 0.59 gm of Compound 1, 2-(dimethylamino)ethyl (S-(R*,S*))-4-((3,3-diethyl-1-(((1-(4-methyl-phenyl)butyl)amino)carbonyl)-4-oxo-2-azetidinyl)oxy)benzoate

| | | | |
|---|---|---|---|
| Analysis: | $C_{30}H_{41}N_3O_5$ | | |
| Calc: | C, 68.81; | H, 7.89; | N, 8.02. |
| Found: | C, 68.85; | H, 8.09; | N, 7.97. |

When N,N-dimethylaminoethanolamine is replaced by the appropriate amino alcohols the correponding esters are obtained.

Compound 13

1-Dimethylamino-2-propyl [S-(R*,S*)]-4-[[3,3-diethyl-1-[[[1-(4-methyl-phenyl)butyl]amino]carbonyl]-4-oxo-2-azetidinyl]oxy]benzoate

| | | | |
|---|---|---|---|
| Analysis: | $C_{31}H_{43}N_3O_5$ | | |
| Calc: | C, 69.25; | H, 8.06; | N, 7.82. |
| Found: | C, 68.97; | H, 8.01; | N, 7.80. |

Compound 14

3-Dimethylamino-1-propyl [S-(R*,S*)]-4-[[3,3-diethyl-1-[[[1-(4-methyl-phenyl)butyl]amino]carbonyl]-4-oxo-2-azetidinyl]oxy]benzoate

| | | | |
|---|---|---|---|
| Analysis: | $C_{31}H_{43}N_3O_5$ | | |
| Calc: | C, 69.25; | H, 8.06; | N, 7.81. |
| Found: | C, 68.85; | H, 8.19; | N, 7.72. |

Compound 16

2-Diethylaminoethyl [S-(R*,S*)]-4-[[3,3-diethyl-1-[[[1-(4-methyl-phenyl)butyl]amino][carbonyl]-4-oxo-2-azetidinyl]oxy]benzoate

| | | | |
|---|---|---|---|
| Analysis: | $C_{32}H_{45}N_3O_6$ | | |
| Calc: | C, 69.66; | H, 8.22; | N, 7.62. |
| Found: | C, 69.37; | H, 8.41; | N, 7.51. |

Compound 17

2-(1-[4-morpholino]ethyl) [S-(R*,S*)]-4-[[3,3-diethyl-1-[[[1-(4-methyl-phenyl)butyl]amino]carbonyl]-4-oxo-2-azetidinyl]oxy]benzoate

| | |
|---|---|
| Analysis: | $C_{32}H_{43}N_3O_6$ |
| Calc: | C, 67.94; H, 7.66; N, 7.43. |
| Found: | C, 67.67; H, 7.90; N, 7.26. |

Compound 18

4-dimethylaminobutyl [S-(R*,S*)]-4-[[3,3-diethyl-1-[[[1-(4-methyl-phenyl)butyl]amino] carbonyl]-4-oxo-2-azetidinyl]oxy]benzoate

| | |
|---|---|
| Analysis: | $C_{32}H_{45}N_3O_5$ + 0.2 $H_2O$ |
| Calc: | C, 69.21; H, 8.24; N, 7.56. |
| Found: | C. 69.35; H, 8.24; N, 7.29. |

Compound 20

2-dimethylamino-2-methyl-1-propyl[S-(R*,S*)]-4-[[3,3-diethyl-1-[[[1-(4-methyl-phenyl)butyl]amino]carbonyl]-4-oxo-2-azetidinyl]oxy]benzoate

| | |
|---|---|
| Analysis: | $C_{32}H_{45}N_3O_5$ |
| Calc: | C, 69.66; H, 8.22; N, 7.62. |
| Found: | C, 69.52; H, 8.47; N, 7.59. |

Compound 21

2-(diisopropylamino)ethyl [S-(R*,S*)]-4-[[3,3-diethyl-1-[[[1-(4-methyl-phenyl)butyl]amino]carbonyl]-4-oxo-2-azetidinyl]oxy]benzoate

| | |
|---|---|
| Analysis: | $C_{34}H_{49}N_3O_5$ |
| Calc: | C, 70.44; H, 8.52; N, 7.25. |
| Found: | C, 70.28; H, 8.76; N, 7.13. |

Compound 22

Benzyl [S-(R*,S*)]-4-[2-[[4-[[3,3-di-ethyl-1-[[[1-(4-methylphenyl)butyl]-amino]carbonyl]-4-oxo-2-azetidinyl]oxy]-benzoyl] oxy]-ethyl]-1-Piperazine-carboxylate

| | |
|---|---|
| Analysis: | $C_{40}H_{50}N_4O_7$ |
| Calc: | C, 68.75; H, 7.21; N, 8.02. |
| Found: | C, 68.39; H, 7.30; N, 7.84. |

Compound 23

2-(dibutylamino)ethyl [S-(R*,S*)]-4-[[3,3-diethyl-1-[[[1-(4-methyl-phenyl)-butyl]amino]carbonyl]-4-oxo-2-azetidinyl]oxy]benzoate.

| | |
|---|---|
| Analysis: | $C_{36}H_{53}N_3O_5$ |
| Calc: | C, 71.14; H, 8.79; N, 6.91. |
| Found: | C, 71.00; H, 9.03; N, 6.81. |

Compound 24

[S-(R*,S*)]-6-(dimethylamino)hexyl-4-[[3,3-diethyl-1-[[[1-(4-methyl-phenyl)-butyl]amino]carbonyl]-4-oxo-2-azetidinyl]oxy]-benzoate

| | |
|---|---|
| Analysis: | $C_{34}H_{49}N_3O_5$ + 1 $H_2O$ |
| Calc: | C, 68.31; H, 8.60; N, 7.03. |
| Found: | C, 68.34; H, 8.29; N, 6.86. |

Compound 26

2-(4-methyl-1-piperazinyl)ethyl[S-(R*,S*)]4-[[3,3-diethyl-1-[[[1-(4-methyl-phenyl)butyl]amino]carbonyl]-4-oxo-2-azetidinyl]oxy]benzoate.

| | |
|---|---|
| Analysis: | $C_{33}H_{46}N_4O_5$ + 0.8 $H_2O$ |
| Calc: | C, 66.82; H, 8.09; N, 9.44. |
| Found: | C, 67.28; H, 8.10; N, 8.96. |

Compound 28

2-(diphenylamino)ethyl[S-(R*,S*)]-4-[[3,3-diethyl-1-[[[1-(4-methylphenyl)-butyl]amino]carbonyl]-4-oxo-2-azetidinyl]oxy]benzoate.

| | |
|---|---|
| Analysis: | $C_{40}H_{45}N_3O_5$ + 1.4 $H_2O$ |
| Calc: | C, 71.40; H, 7.16; N, 6.25. |
| Found: | C, 71.62; H, 6.99; N, 5.99. |

Compound 29

2-(di-2-propenylamino)ethyl [S-(R*,S*)]-4-[[3,3-diethyl-1-[[[1-(4-methylphenyl)-butyl]amino]carbonyl]-4-oxo-2-azetidinyl]oxy]benzoate.

| | |
|---|---|
| Analysis: | $C_{34}H_{45}N_3O_5$ |
| Calc: | C, 70.93; H, 7.88; N, 7.30. |
| Found: | C, 71.18; H, 8.06; N, 7.34. |

Compound 30

2-(dimethylamino)-2-phenylethyl [S-(R*,-S*)]-4-[[3,3-diethyl-1-[[[1-(4-methyl-phenyl)butyl]amino]carbonyl]-4-oxo-2-azetidinyl] oxy]benzoate.

| | |
|---|---|
| Analysis: | $C_{36}H_{45}N_3O_5$ |
| Calc. | C, 72.09; H, 7.56; N, 7.00. |
| Found: | C, 71.75; H, 7.67; N, 6.70. |

Compound 31

2-[methyl(phenylmethyl)amino]ethyl [S-(R*,S*)]-4-[[3,3-diethyl-1-[[[1-(4-methyl-phenyl)butyl]amino]carbonyl]-4-oxo-2-azetidinyl]oxy]benzoate.

When [S-(R*,S*)]-4-[[3,3-diethyl-1-[[[1-(4-methylphenyl) butyl]amino]carbonyl]-4-oxo-2-azetidinyl] oxy]-2,6-dimethyl benzoic acid is used in place of [S(R*, S*)]-4-[[3,3-diethyl-1-[[[1-(4-methylphenyl)-butyl]amino] carbonyl]-4-oxo-2-azetidinyl]oxy]benzoic acid in the procedure of Example 3A and allowed to react with the appropriate amino alcohols the following esters are obtained.

Compound 304

2-(dimethylamino)ethyl [S,(R*,S*)]-4-[[3,3-diethyl-1-[[[1-(4-methylphenyl)-butyl]amino]carbonyl]-4-oxo-2-azetidinyl]oxy]-2,6-dimethyl-benzoate.

Compound 305

2-(diethylamino)ethyl [S-(R*,S*)]-4-[[3,3-diethyl-1-[[[1-(4-methylphenyl)-butyl]amino]carbonyl]-4-oxo-2-azetidinyl]oxy]-2,6-dimethyl-benzoate.

Compound 306

2-[bis(1-methylethyl)amino]-ethyl [S-(R*S*)]4-[[3,3-diethyl-1-[[[1-(4-methylphenyl)butyl]amino]carbonyl]-4-oxo-2-azetidinyl]oxy]-2,6-dimethylbenzoate.

Treatment of the acid [S-(R*,S*)]-4-[[3,3-diethyl-1-[[[1-(4-methylphenyl)butyl]amino]carbonyl]-4-oxo-2-azetidinyl]oxy]benzeneacetic acid with oxalyl chloride according to the procedure of Example 3A affords the corresponding acid chloride which when allowed to react with the appropriate amino alcohol according to the procedure of Example 8 gives the following amino esters:

Compound 32

| | |
|---|---|
| Analysis: | $C_{31}H_{43}N_3O_5$ |
| Calc: | C, 69.25; H, 8.06; N, 7.82. |
| Found: | C, 69.02; H, 7.86; N, 7.74. |

Compound 33

| | |
|---|---|
| Analysis: | $C_{32}H_{45}N_3O_5$ |
| Calc: | C, 69.66; H, 8.22; N, 7.62. |
| Found: | C, 69.10; H, 8.17; N, 7.50. |

Compound 34

| | |
|---|---|
| Analysis: | $C_{33}H_{47}N_3O_5$ |
| Calc: | C, 70.06; H, 8.38; N, 7.43. |
| Found: | C, 69.70; H, 8.41; N, 7.05. |

Compound 35

| | |
|---|---|
| Analysis: | $C_{33}H_{45}N_3O_6$ |
| Calc: | C, 68.37; H, 7.82; N, 7.25. |
| Found: | C, 68.55; H, 8.19; N, 7.08. |

Compound 36

| | |
|---|---|
| Analysis: | $C_{32}H_{45}N_3O_5$ |
| Calc: | C, 69.66; H, 8.22; N, 7.62. |
| Found: | C, 69.60; H, 8.49; N, 7.55. |

EXAMPLE 9

To a solution of 0.247 g of Compound 1 in 2 ml of ethyl acetate is added 0.125 gm of m-chloroperoxy benzoic acid. After 30 minutes at room temperature the reaction mixture is concentrated in vacuo. Chromatography of the residue on silica gel using methylene chloride/methanol/water 85/15/1.5 gives the desired N-oxide Compound 15.

| | |
|---|---|
| Analysis: | $C_{30}H_{41}N_3O_8 + 1.4\ H_2O$ |
| Calc: | 63.79; H, 7.82; N, 7.44 |
| Found: | 63.89; H, 7.85; N, 7.27 |

EXAMPLE 10

[S-(R*,S*)] 2-[4-[[[2-(dimethylamino)-ethyl]amino]-carbonyl]phenoxy]-3,3-diethyl-N-[1-(4-methylphenyl)-butyl]-4-oxo-1-azetidinecarboxamide.

To a solution of 0.104 g carbonyldiimidazole in 2 ml methylene chloride is added a solution of 0.227 g of [S-(R*,S*)]-4-((3,3-diethyl-1-((-1-(4-methylphenyl) butylamino)carbonyl)-4-oxo-2-azetidinyl)-oxy)benzoic acid in 3 ml methylene chloride. The mixture is stirred at ambient temperature for 30 minutes at which time 0.100 g of N,N-dimethylethylenediamine is added. After stirring overnight at room temperature the reaction mixture is poured into benzene (50 ml) and washed with water. The organic layer is separated, dried through sodium sulfate and concentrated in vacuo. Silica gel chromatography using 5% methanol in methylene chloride yields 0.160 g of 2-[4-[[[2-(dimethylamino)-ethyl]amino]carbonyl]phenoxy]-3,3-diethyl-N-[1-(4-methylphenyl)butyl]-4-oxo-1-azetidinecarboxamide. (Compound 73).

| | |
|---|---|
| Analysis: | $C_{30}H_{42}N_4O_4$ + 0.4 $H_2O$ |
| Calc: | C, 68.00; H, 8.14; N, 10.57. |
| Found: | C, 68.01; H, 8.18; N, 10.62. |

EXAMPLE 11

A. (S-(R*,S*))-4-((3,3-diethyl-1-((1-(4-methylphenyl)butylamino)carbonyl)-4-oxo-2-azetidinyl)-oxy)-benzoyl chloride.

To a solution of 0.150 g of [S-(R*,S*)] 4-((3,3-diethyl-1-(((1-(4-methylphenyl)butyl)amino)-carbonyl)-4-oxo-2-azetidinyl)oxy)benzoic acid in 5 ml methylene chloride containing a catalytic amount of dimethylformamide is added 0.5 ml of oxalyl chloride. The mixture is stirred at room temperature for 30 minutes and then concentrated in vacuo to yield (S-(R*,S*))-4-((3,3-diethyl-1-((1-(4-methylphenyl)-butylamino)carbonyl)-4-oxo-2-azetidinyl)oxy)-benzoyl chloride.

B. [S-(R*,S*)]2-[4-[[[2-(dimethylamino)ethyl] methyl-amino]carbonyl]-phenoxy]-3,3-diethyl-N-[1-(4-methylphenyl]butyl]-4-oxo-1-azetidinecarboxamide.

The above acid chloride is dissolved in 3 ml methylene chloride and a solution of 0.20 gm of N,N,N'-trimethylethylenediamine in 2 ml methylene chloride is added. The mixture is stirred overnight and then concentrated in vacuo. The residue is extracted between ethyl acetate and saturated sodium bicarbonate solution. The organic layer is dried through sodium sulfate and concentrated in vacuo. Silica gel chromatography of the residue (5% methanol in methylene chloride) affords 0.117 g of [S-(R*,S*)]-2-[4-[[[2-(dimethylamino)ethyl]methylamino] carbonyl]-phenoxy]-3,3-diethyl-N-[1-(4-methylphenyl] butyl-4-oxo-1-azetidinecarboxamide. (Compound 75).

| | |
|---|---|
| Analysis: | $C_{31}H_{44}N_4O_4$ + 0.5$H_2O$ |
| Calc: | C, 68.23; H, 8.31; N, 10.27. |
| Found: | C, 68.20; H, 8.41; N, 10.10. |

When N,N,N'-trimethylethylenediamine of Example 11b is replaced by the appropriate amines, there is obtained the corresponding amides.

1) Compound 76

| | |
|---|---|
| Analysis: | $C_{32}H_{46}N_4O_4$ |
| Calc: | C, 69.79; H, 8.42; N, 10.17. |
| Found: | C, 69.02; H, 8.60; N, 9.54. |

2) Compound 77

| | |
|---|---|
| Analysis: | $C_{32}H_{46}N_4O_4$ + 0.75 $H_2O$ |
| Calc: | C, 68.12; H, 8.49; N; 9.93. |
| Found: | C, 68.22; H, 8.48; N, 10.17. |

3) Compound 78

| | |
|---|---|
| Analysis: | $C_{32}H_{44}N_4O_5$ |
| Calc: | C, 68.06; H, 7.85; N, 9.92. |
| Found: | C, 67.84; H, 8,07; N, 9.62. |

4) Compound 79

| | |
|---|---|
| Analysis: | $C_{33}H_{46}N_4O_5$ + $H_2O$ |
| Calc: | C, 66.42; H, 8.11; N, 9.39. |
| Found: | C, 66.73; H, 8.19; N, 9.23. |

5) Compound 80

| | |
|---|---|
| Analysis: | $C_{35}H_{52}N_4O_6$ |
| Calc: | C, 67.28; H, 8.39; N, 8.97. |
| Found: | C, 67.08; H, 8.77; N, 8.41. |

6) Compound 81

| | |
|---|---|
| Analysis: | $C_{33}H_{48}N_4O_4$ + $H_2O$ |
| Calc: | C, 68.01; H, 8.65; N, 9.61. |
| Found: | C, 68.42; H, 8.59; N, 9.17. |

7) Compound 82

| | |
|---|---|
| Analysis: | $C_{36}H_{46}N_4O_4$ + 0.5$H_2O$ |
| Calc: | C, 71.14; H, 7.79; N, 9.21. |
| Found: | C, 71.41; H, 7.68; N, 9.10. |

8) Compound 83

| | |
|---|---|
| Analysis: | $C_{32}H_{46}N_4O_4$ + 1.2$H_2O$ |
| Calc: | C, 67.15; H, 8.52; N, 9.79. |
| Found: | C, 67.21; H, 8.26; N, 9.47. |

9) Compound 84

10) Compound 86

| | |
|---|---|
| Analysis: | $C_{35}H_{52}N_4O_4$ |
| Calc: | C, 70.91; H, 8.84; N, 9.45. |
| Found: | C, 70.37; H, 8.84; N, 8.77. |

11) Compound 89

| | |
|---|---|
| Analysis: | $C_{31}H_{39}N_5O_4$ + 0.7$H_2O$ |
| Calc: | C, 66.71; H, 7.29; N, 12.54. |
| Found: | C, 66.91; H, 7.40; N, 12.14. |

12) Compound 90

| | |
|---|---|
| Analysis: | $C_{33}H_{46}N_4O_4$ + 0.8$H_2O$ |
| Calc: | C, 68.67; H, 8.31; N, 9.70. |
| Found: | C, 68.82; H, 8.11; N, 9.70. |

13) Compound 91

| | |
|---|---|
| Analysis: | $C_{34}H_{48}N_4O_4$ + 0.3$H_2O$ |
| Calc: | C, 70.11; H, 8.41; N, 9.61. |
| Found: | C, 70.17; H, 8.64; N, 9.33. |

14) Compound 92

| | |
|---|---|
| Analysis: | $C_{30}H_{42}N_4O_4$ + 1.2$H_2O$ |
| Calc: | C, 66.14; H, 8.22; N, 10.29. |
| Found: | C, 66.18; H, 8.12; N, 10.31. |

15) Compound 93

| | |
|---|---|
| Analysis: | $C_{32}H_{44}N_4O_6$ + 0.3$H_2O$ |
| Calc: | C, 65.57; H, 7.67; N, 9.56. |
| Found: | C, 65.72; H, 7.50; N, 9.34. |

16) Compound 94

| | |
|---|---|
| Analysis: | $C_{32}H_{44}N_4O_4$ + 0.3$H_2O$ |
| Calc: | C, 70.04; H, 8.08; N, 10.21. |
| Found: | C, 70.34; H, 8.90; N, 8.93. |

17) Compound 95

| | |
|---|---|
| Analysis: | $C_{33}H_{46}N_4O_4$ + .5$H_2O$ |
| Calc: | C, 69.32; H, 8.28; N, 9.80. |
| Found: | C, 69.41; H, 8.25; N, 9.58. |

18) Compound 99

| | |
|---|---|
| Analysis: | $C_{38}H_{54}N_4O_4$ + 1.5$H_2O$ |
| Calc: | C, 69.37; H, 8.72; N, 8.51 |
| Found: | C, 69.48; H, 8.44; N, 8.36 |

19) Compound 102

| | |
|---|---|
| Analysis: | $C_{40}H_{49}N_5O_6$ + 1.0 $H_2O$ |
| Calc: | C, 67.30; H, 7.20; N, 9.81 |
| Found: | C, 67.50; H, 7.24; N, 9.53 |

20) Compound 104

| | |
|---|---|
| Analysis: | $C_{32}H_{41}N_5O_4$ + 0.75$H_2O$ |
| Calc: | C, 67.04; H, 7.47; N, 12.21. |
| Found: | C, 67.16; H, 7.56; N, 11.95. |

21) Compound 105

| | |
|---|---|
| Analysis: | $C_{32}H_{44}N_4O_5$ + 0.5$H_2O$ |
| Calc: | C, 66.99; H, 7.91; N, 9.77. |
| Found: | C, 67,00; H, 8.25; N, 9.50. |

22) Compound 106

| | |
|---|---|
| Analysis: | $C_{32}H_{45}N_5O_5$ + 0.8$H_2O$ |
| Calc: | C, 64.69; H, 7.90; N, 11.78. |
| Found: | C, 64.93; H, 8.25; N, 11.12. |

23) Compound 107

| | |
|---|---|
| Analysis: | $C_{31}H_{44}N_3O_6S$ + 0.3$H_2O$ |
| Calc: | C, 61.42; H, 7.41; N, 9.24. |
| Found: | C, 61.43; H, 7.54; N, 9.05. |

24) Compound 110

| | |
|---|---|
| Analysis: | $C_{35}H_{44}N_4O_4$ |
| Calc: | C, 71.89; H, 7.58; N, 9.58. |
| Found: | C, 71.65; H, 7.55; N, 9.34. |

25) Compound 111

| | | | |
|---|---|---|---|
| Analysis: | $C_{34}H_{42}N_4O_4$ + 0.5$H_2O$ | | |
| Calc: | C, 70.44; | H, 7.47, | N, 9.66. |
| Found: | C, 70.82, | H, 7.46; | N, 9.20. |

26) Compound 113

| | | | |
|---|---|---|---|
| Analysis: | $C_{34}H_{42}N_4O_4$ + 0.3$H_2O$ | | |
| Calc: | C, 70.88; | H, 7.45; | N, 9.72. |
| Found: | C, 71.12; | H, 7.44; | N, 9.32. |

27) Compound 115

| | | | |
|---|---|---|---|
| Analysis: | $C_{34}H_{42}N_4O_4$ + 0.7$H_2O$ | | |
| Calc: | C, 69.99; | H, 7.50; | N, 9.60. |
| Found: | C, 70.14, H, 7.63; N, 9.25. | | |

28) Compound 116

| | | | |
|---|---|---|---|
| Analysis: | $C_{34}H_{46}N_4O_4$ + 1.4$H_2O$ | | |
| Calc: | C, 68.06; | H, 8.19; | N, 9.33. |
| Found: | C, 68.40; | H, 8.14; | N, 8.87. |

29) Compound 117

| | | | |
|---|---|---|---|
| Analysis: | $C_{40}H_{51}N_5O_6$ + 0.6$H_2O$ | | |
| Calc: | C, 67.79; | H, 7.42; | N, 9.88. |
| Found: | C, 67.81; | H, 7.58; | N, 9.76. |

30) Compound 118

| | | | |
|---|---|---|---|
| Analysis: | $C_{33}H_{47}N_5O_4$ + 0.7$H_2O$ | | |
| Calc: | C, 67.14; | H, 8.26; | N, 11.86 |
| Found: | C, 67.54; | H, 8.51; | N, 11.28. |

31) Compound 119

| | | | |
|---|---|---|---|
| Analysis: | $C_{35}H_{48}N_4O_4$ + 1.25$H_2O$ | | |
| Calc: | C, 68.76; | H, 8.32; | N, 9.16. |
| Found: | C, 69.07; | H, 8.19; | N, 8.75. |

32) Compound 121

| | | | |
|---|---|---|---|
| Analysis: | $C_{34}H_{48}N_4O_4$ + $1H_2O$ | | |
| Calc: | C, 68.66; | H, 8.47; | N, 9.42. |
| Found: | C, 69.02; | H, 8.32; | N, 9.06. |

33) Compound125

| | | | |
|---|---|---|---|
| Analysis: | $C_{37}H_{48}N_4O_4$ + $0.5H_2O$ | | |
| Calc: | C, 71.47; | H, 7.94; | N, 9.01 |
| Found: | C, 71.65; | H, 7.91; | N, 8.73. |

34) Compound 126

| | | | |
|---|---|---|---|
| Analysis: | $C_{41}H_{54}N_4O_5$ + $2H_2O$ | | |
| Calc: | C, 68.83; | H, 8.25; | N, 7.64. |
| Found: | C, 69.03; | H, 7.79; | N, 7.50. |

35) Compound 132

| | | | |
|---|---|---|---|
| Analysis: | $C_{35}H_5ON_4O_4$ | | |
| Calc: | C, 71.15; | H, 8.53; | N, 9.48. |
| Found: | C, 70.90; | H, 8.74; | N, 9.12. |

36) Compound 133

| | | | |
|---|---|---|---|
| Analysis: | $C_{40}H_{52}N_4O_4$ + $0.9H_2O$ | | |
| Calc: | C, 71.80; | H, 8.10; | N, 8.37. |
| Found: | C, 71.86; | H, 8.17; | N, 8.18. |

37) Compound 137

| | | | |
|---|---|---|---|
| Analysis: | $C_{37}H_{48}N_4O_4$ + $0.8H_2O$ | | |
| Calc. | C, 70.85; | H, 7.97; | H, 8.93. |
| Found: | C, 71.01; | H, 7.97; | N, 8.54. |

38) Compound 139

| | | | |
|---|---|---|---|
| Analysis: | $C_{39}H_{51}N_5O_4$ + $0.8H_2O$ | | |
| Calc: | C, 70.09; | H, 7.93; | N, 10.48. |
| Found: | C, 70.18; | H, 7.79; | N, 10.42. |

39) Compound 142

| | | | |
|---|---|---|---|
| Analysis: | $C_{38}H_{55}N_5O_6$ | | |
| Calc: | C, 67.33; | H, 8.18; | N, 10.33. |
| Found: | C, 67.02; | H, 8.31; | N, 9.89. |

40) Compound 143

| | | | |
|---|---|---|---|
| Analysis: | $C_{34}H_{51}N_5O_4$ | | |
| Calc: | C, 68.77; | H, 8.66; | N, 11.80. |
| Found: | C, 68.57; | H, 8.50; | N, 11.53 |

41) Compound 144

| | | | |
|---|---|---|---|
| Analysis: | $C_{38}H_{59}N_5O_4$ + $0.4H_2O$ | | |
| Calc: | C, 69.45; | H, 9.17; | N, 10.65. |
| Found: | C, 69.69; | H, 9.02; | N, 10 35. |

42) Compound 145

| | | | |
|---|---|---|---|
| Analysis: | $C_{36}H_{47}N_5O_4$ + $H_2O$ | | |
| Calc: | C, 68.44; | H, 7.82; | N, 11.08 |
| Found: | C, 68.69; | H, 7.74; | N, 10.76. |

43) Compound 148

| | | | |
|---|---|---|---|
| Analysis: | $C_{36}H_{47}N_5O_4$ + $0.4H_2O$ | | |
| Calc: | C, 69.62; | H, 7.56; | N, 11.27. |
| Found: | C, 69.79; | H, 7.70; | N, 11.12. |

44) Compound 149

| | | | |
|---|---|---|---|
| Analysis: | $C_{39}H_{50}N_4O_4$ + $0.4H_2O$ | | |
| Calc: | C, 72.50; | H, 7.93; | N, 8.67 |
| Found: | C, 72.44; | H, 7.99; | N, 8.87. |

45) Compound 150

| | | | |
|---|---|---|---|
| Analysis: | $C_{36}H_{47}N_5O_4$ + $0.3H_2O$ | | |
| Calc. | C, 69.83; | H, 7.74; | N, 11.31. |
| Found: | C, 69.93; | H, 7.65, | N, 11.10. |

46) Compound 151

| | | | |
|---|---|---|---|
| Analysis: | $C_{33}H_{47}N_5O_4$ | | |
| Calc: | C, 68.60; | H, 8.20; | N, 12.12. |
| Found: | C, 68.40; | H, 8.16; | N, 11.90. |

47) Compound 245

| | | | |
|---|---|---|---|
| Analysis: | $C_{36}H_{44}N_4O_4$ | | |
| Calc: | C, 72.46; | H, 7.43; | N, 9.39 |
| Found: | C, 72.49; | H, 7.49; | N, 9.25 |

48) Compound 246

| | | | |
|---|---|---|---|
| Analysis: | $C_{37}H_{46}N_4O_4$ + $0.25H_2O$ | | |
| Calc: | C, 72.26; | H, 7.61; | N, 9.10. |
| Found: | C, 72.35; | H, 7.83; | N, 8.73. |

49) Compound 154

| | |
|---|---|
| Analysis: | $C_{35}H_{48}N_4O_4$ + $0.8H_2O$ |
| Calc: | C, 69.70; H, 8.29; N, 9.29 |
| Found: | C, 69.65; H, 8.27, N, 9.35. |

50) Compound 158

| | |
|---|---|
| Analysis: | $C_{35}H_{48}N_4O_4$ + $0.5H_2O$ |
| Calc: | C, 73.29; H, 7.65; N, 8.33. |
| Found: | C, 73.71, H, 7.75, N, 7.75. |

51) Compound 159

| | |
|---|---|
| Analysis: | $C_{35}H_{48}N_4O_4$ |
| Calc: | C, 73.09; H, 7.66; N, 8.31. |
| Found: | C, 73.40; H, 7.75; N, 7.80. |

52) Compound 160

| | |
|---|---|
| Analysis: | $C_{38}H_{48}N_4O_4$ + $1.0H_2O$ |
| Calc: | C, 70.78; H, 8.12; N, 8.68. |
| Found: | C, 71.00; H, 8.05; N, 8.59. |

53) Compound 161

| | |
|---|---|
| Analysis: | $C_{43}H_{52}N_4O_4$ + $1H_2O$ |
| Calc: | C, 73.05; H, 7.70; N, 7.92. |
| Found: | C, 73.29; H, 7.95; N, 7.37. |

54) Compound 166

| | |
|---|---|
| Analysis: | $C_{33}H_{46}N_4O_4$ + $1.5H_2O$ |
| Calc. | C, 67.20; H, 8.37; N, 9.50 |
| Found: | C, 67.38; H, 7.98; N, 9.41. |

55) Compound 171

| | |
|---|---|
| Analysis: | $C_{36}H_{52}N_4O_6$ + $1.6H_2O$ |
| Calc: | C, 64.95; H, 8.36; N, 8.41. |
| Found: | C, 65.26; H, 8.15; N, 8.07. |

56) Compound 177

| | |
|---|---|
| Analysis: | $C_{38}H_{47}N_5O_4$ |
| Calc: | C, 71.56; H, 7.43; N, 10,98. |
| Found: | C, 71.64; H, 7.62; N, 10.93. |

57) Compound 178

| | |
|---|---|
| Analysis: | $C_{38}H_{50}N_4O_4$ |
| Calc: | C, 72.81; H, 8.04; N, 8.94. |
| Found: | C, 72.96; H, 8.17; N, 8.83. |

58) Compound 179

| | |
|---|---|
| Analysis: | $C_{38}H_{47}N_5O_4$ |
| Calc: | C, 71.56; H, 7.43; N, 10.98. |
| Found: | C, 72.00; H, 7.55; N, 10.87. |

59) Compound 180

| | |
|---|---|
| Analysis: | $C_{38}H_{47}F_3N_4O_4$ |
| Calc: | C, 67.04; H, 6.96; N, 8.23. |
| Found: | C, 67.02; H, 7.25; N, 8.23. |

60) Compound 181

| | |
|---|---|
| Analysis: | $C_{38}H_{47}F_3N_4O_4$ |
| Calc: | C, 67.04; H, 6.96; N, 8.23 |
| Found: | C, 66.63; H, 6.98; N, 7.94. |

61) Compound 182

| Analysis: | $C_{37}H_{47}F\ N_4O_4$ |
|---|---|
| Calc: | C, 70.45; H, 7.51; N, 8.88 |
| Found: | C, 70.28; H, 7.74; N, 8.82. |

62) Compound 185

| Analysis: | $C_{34}H_{48}N_4O_4$ |
|---|---|
| Calc: | C, 70.80; H, 8.39; N, 9.71 |
| Found: | C, 70.44; H, 8.45; N, 9.51. |

63) Compound 186

| Analysis: | $C_{37}H_{48}N_4O_4$ +$0.8H_2O$ |
|---|---|
| Calc: | C, 70.85; H, 7.97; N, 8.93 |
| Found: | C, 71.12; H, 8.25; N, 8.45. |

64) Compound 191

| Analysis: | $C_{42}H_{51}N_5O_4$ +.$5CH_2C1_2$ |
|---|---|
| Calc: | C, 69.78; H, 7.16; N, 9.58 |
| Found: | C, 69.75; H, 7.31; N, 9.68. |

65) Compound 203

| Analysis: | $C_{37}H_{47}N_4O_4$ +$1.1H_2O$ |
|---|---|
| Calc: | C, 68.31; H, 7.62; N, 8.61 |
| Found: | C, 68.32; H, 7.57; N, 8.53. |

66) Compound 204

| Analysis: | $C_{37}H_{47}ClN_4O_4$ |
|---|---|
| Calc: | C, 68.66; H, 7.32; N, 8.66. |
| Found: | C, 68.32, H, 7.48; N, 8.42. |

67) Compound 205

| Analysis: | $C_{38}H_{50}N_4O_5$ +0.7$H_2O$ |
|---|---|
| Calc: | C, 69.63; H, 7.90; N, 8.54. |
| Found: | C, 69.72; N, 7.91; N, 8.54. |

68) Compound 206

| Analysis: | $C_{39}H_{52}N_4O_6$ +0.8$H_2O$ |
|---|---|
| Calc: | C, 68.15; H, 7.86; N, 8.15 |
| Found: | C, 68.01; H, 8.02; N, 8.15. |

EXAMPLE 12

A) [S-(R*,S*)3,3-Diethyl-2-[4-[[[2-(4-hydroxy-1-piperidinyl)ethyl]amino]carbonyl]phenoxy]-N-[1-(4-methylphenyl)butyl]-4-oxo-1-azetidinecarboxamide When 1-(2-aminoethyl)-4-benzyloxypiperidine is used in place of N,N,N'-trimethylethylene diamine in the procedure of Example 11b there is obtained [S-(R*,S*)]3,3-diethyl-2-[4-[[[2-(4-benzyloxy-1-piperidinyl]ethyl]amino]carbonyl]phenoxy]-N-[1-(4-methylphenyl)butyl]-4-oxo-1-azetidinecarboxamide.

B) [S-(R+,S*)]3,3-diethyl-2-[4-[[[2-(4-hydroxy-1-piperidinyl)ethyl]amino]carbonyl]phenoxy]-N-[1-(4-methyl-phenyl)butyl]-4-oxo-1-azetidine-carboxamide A solution of the amide from step A above in 10 ml of glacial acetic acid containing 22 mg of 10% Pd/C is hydrogenated under 42 lb hydrogen pressure. When TLC indicate completion of the reaction, the mixture is filtered and concentrated in vacuo after the addition of 50 ml toluene. The residue is dissolved in ethyl acetate, washed with saturated sodium bicarbonate solution. The organic layer is dried with sodium sulfate and concentrated in vacuo. The residue is chromatographed on 15 g silica gel using 5% methanol in methylene chloride and yields 96 mg of

[S-(R+,S*)]-3,3-diethyl-2-[4-[[[2-(4-hydroxy-1-piperidinyl)ethyl]amino]carbonyl]phenoxy]-N-[1-(4-methyl-phenyl)butyl]-4-oxo-1-azetidine-carboxamide

| Analysis: | $C_{33}H_{46}N_4O_5$ +1.3$H_2O$ |
|---|---|
| Calc: | C, 65.83; H, 8.13; N, 9.30 |
| Found: | C, 66.10; H, 8.06; N, 8.91 |

When 1-(2-aminoethyl)-4-benzyloxypiperidine is replaced in the procedure of Example 12 by the appropriate amines, the following compounds 123, 124, 129, 131 and 138 are obtained, for example:

1) Compound 129

| Analysis: | $C_{34}H_{48}N_4O_5$ |
|---|---|
| Calc: | C, 68.89; H, 8.16; N, 9.45 |
| Found: | C, 68.68; H, 8.18; N, 8.65 |

2) Compound 131

| Analysis: | $C_{32}H_{44}N_4O_5$ +1$H_2O$ |
|---|---|
| Calc: | C, 65.92; H, 7.96; N, 9.61 |
| Found: | C, 66.07; H, 7.86; N, 9.45 |

3) Compound 138

| Analysis: | $C_{33}H_{46}N_4O_5$ +0.5$H_2O$ |
|---|---|
| Calc: | C, 67.43; H, 8.06; N, 9.53 |
| Found: | C, 67.61; H, 8.06; N, 9.37 |

Diamine Intermediates

The diamines used to prepare the amino amides described herein were commercially available or prepared according to the following routes

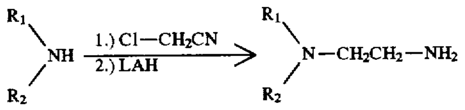

EXAMPLE 13

A N-cyanomethylhomopiperazine.

To a solution of 1.98 g homopiperazine in 50 ml acetone is added 4.25 g of powdered anhydrous sodium carbonate and 1.3 ml of chloroacetonitrite. After 24 hrs the reaction mixture is filtered and the filter cake washed with 100 ml acetone. The combined filtrates are concentrated in vacuo and the residue chromatographed on silica gel using methylene chloride as the eluent. The yield of N-cyanomethyl homopiperazine is 2.69 g.

B. N-(2-aminoethyl)homopiperazine.

To a suspension of 1.02 g lithium aluminum hydride in 50 ml of ether is slowly added a solution of 2.65 gm N-cyanomethyl homopiperazine in 25 ml ether. After the addition in complete the mixture is heated at reflux for 1 hour, then cooled to room temperature and quenched carefully with 1 ml water, 1 ml of 15% sodium hydroxide solution and 3 ml water. The mixture is filtered through sodium sulfate, the filter cake washed well with ether and the combined filtrates concentrated in vacuo to yield 2.60 g. N-(2-aminoethyl)homopiperazine.

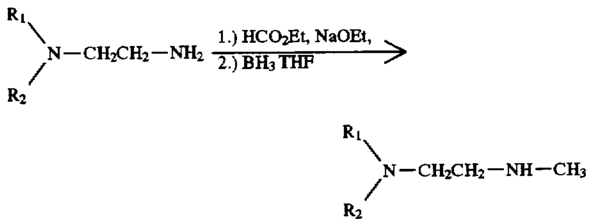

EXAMPLE 14

N-(2-methylaminoethyl)homopiperazine.

A). N-(2-formamidoethyl)homopiperazine.

To a carefully prepared solution of 0.718 g of 60% sodium hydride dispension in 75 ml of absolute ethanol which has been cooled to 0° C. is added 7.3 ml of ethyl formate. After 5 minutes there is added a solution of 2.55 gm of N-(2-aminoethyl)homopiperazine in 25 ml absolute ethanol. The mixture is stirred at room temperature overnight. Saturated sodium bicarbonate solution (15 ml) is then added and the reaction mixture is stirred with 150 ml ethyl acetate, filtered through $MgSO_4$ and the filtrate concentrated in vacuo. Chromatography of the residue on 150 gm silica gel using an eluent of methylene chloride/methanol/conc. ammonium hydroxide (95/5/0.5) gives 2.78 g of N-(2-formamidoethyl) homopiperazine.

B). N-(2-methylaminoethyl)homopiperazine.

To a solution of 2.75 gm of N-(2-formamidoethyl) homopiperazine in 20 ml of dry THF under $N_2$ is added carefully 60 ml of borane THF solution. After the addition is complete the reaction mixture is heated to reflux for 5 hours then stirred at room temperature overnight. The reaction mixture is quenched by the careful addition of 20 ml of 6N HCl followed by refluxing for 1 hour. The reaction mixture is cooled, 50 ml of water added and solid KOH added carefully to alkaline pH. Extraction with ether gives the desired product N-(2-methylamino)homopiperazine.

EXAMPLE 15

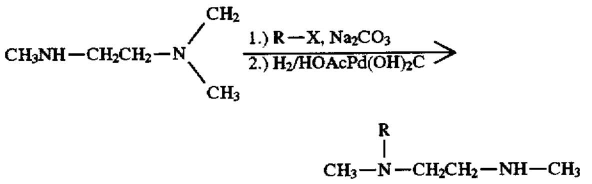

A) N-benzyl-N,N'-dimethyl-N'-(2-phenylethyl)-ethylenediamine

A mixture of 0.900 gm N-benzyl-N,N'-dimethylethylenediamine, 1.10 gm powdered sodium carbonate and 0.75 ml of 2-phenylethylbromide is refluxed for 5 hours. An additional 0.25 ml of bromide is added during this time. The reaction mixture is then cooled and filtered. The filterate is concentrated in vacuo and the residue chromatographed on silica gel using an eluent of $CH_2Cl_2$/$CH_3OH$/$NH_4OH$ (97/3/0.3) to yield 0.875 gm of N-benzyl-N,N'-dimethyl-N'-(2-phenylethyl)ethylenediamine.

B) N,N'-dimethyl-N-(2-phenylethyl) ethylenediamine.

To a solution 0.870 gm N-benzyl-N-N'-di-methyl-N'-(2-phenylethyl)ethylenediamine in 10 ml ethanol and 5 ml acetic acid is added 0.18 gm Pd $(OH)_2$/C. The mixture is hydrogenated at 40 psi for 3.5 hours, then filtered and concentrated in vacuo. The residue is made akaline with 1N NaOH and extracted well with ethyl acetate (5×25 ml). The combined extracts are filtered through sodium sulfate and concentrated to yield N,N'-dimethyl-N-(2-phenyl-ethyl) ethylenediamine.

EXAMPLE 16

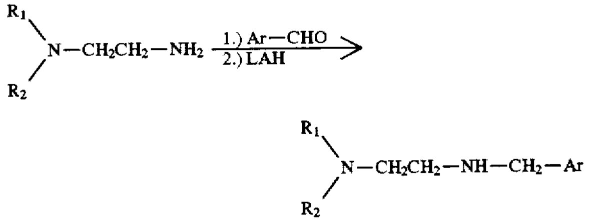

A)

A solution of 1.28 gm 1-(2-amino-ethyl)piperdine and 1.07 gm pyridine-3-carboxaldehyde in 40 ml of toluene is heated to reflux under a Dean Stark trap. After 10 ml toluene distilled over the NMR of an aliquot indicated no aldehyde left. The reaction mixture was concentrated and the imine used directly in the next step.

B)

To a suspension of 0.380 gm of lithium aluminum hydride in 30 ml of dry THE which has been cooled to −10° C. is added dropwise a solution of the above imine in 20 ml of dry THE. After about 1 hour the cold reaction mixture is quenched by the addition of 5 ml of 5N NaOH, then diluted with 100 ml ether and 20 ml of water. The organic layer is separated, washed with brine, filtered thru sodium sulfate and concentrated to give 2.17 gm of 1-[2-(3-pyridyl-methylamino)ethyl]-piperidine suitable for use in subsequent reactions.

EXAMPLE 17

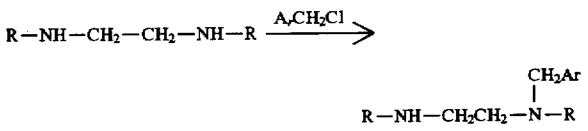

To 7.50 gm of N,N'-dimethylethylenediamine which has been cooled in an ice-ethanol bath is added portionwise over a 30 minute period 1.40 gm of 3-picolyl chloride. After stirring cold for 1 hour after the addition is completed, the reaction mixture is concentrated in vacuo and the residue partitioned between 50 ml of ether and 10 ml of 5N NaOH solution. The organic layer is separated and the aqueous layer extracted 2 times with 50 ml of ether. The combined organic extracts are dried through sodium sulfate and concentrated in vacuo. Chromatography on 150 gm silica gel using $CH_2Cl_2$/$CH_3OH$/$NH_{4OH}$ (90/10/1) as eluent gives 0.930 g of N,N'-dimethyl-N-(3-pyridylmethyl) ethylenediamine.

EXAMPLE 18

Amino Acid→diamine

A)

To an ice cooled solution of 2.29 N-CBZ-D-Proline in 50 ml of $CHCl_2$ is added 1.35 gm 1-hydroxybenzotriazole hydrate followed by 2.06 gm of dicyclohexylcarbodiimide. After 20 minutes, 0.85 ml of pyrrolidine is added and the reaction mixture stirred overnight after which time it is filtered and the filtrate concentrated in vacuo. The residue is partitioned between 100 ml ethyl acetate and 50 ml of 2N hydrochloric acid. The organic layer is separated, washed with 50 ml of 1.0N sodium hydroxide solution, dried through sodium sulfate and concentrated in vacuo. Chromatography on 150 gm of silica gel using ethylacetate in hexanes (30–100%) as eluent gives 2.04 gm of the desired pyrrolidine amide

B)

To a solution of 1.519 gm of the amide (prepared in A) in 20 ml absolute ethanol is added 75 mg of 10% Pd on carbon catalyst. The mixture is hydrogenated at 40 psi for about an hour then filtrate and the filtrate concentrated to yield D-proline pyrrolidine amide.

C)

To a suspension of 0.380 gm of lithium aluminum hydride in 15 ml of dry tetrahydrofuran is carefully added a solution of the D-proline amide (prepared in B above) in 10 ml tetrahydrofuran. The mixture is refluxed for 2 hrs then cooled and quenched with 2 ml of 2.5N sodium hydroxide. The mixture is filtered through a pad of sodium sulfate and the filter cake washed with 2×50 ml of ether. The combined filtrates are concentrated in vacuo to yield 0.80 gm of desired 2-(1-pyrrolidinylmethyl) pyrrolidine.

EXAMPLE 19

[S-(R*,S*)]-2-[4-[[(4-Methyl)piperazin-1-yl] carbonyl]phenoxy]-((3,3-diethyl-N-[1-(methylphenyl)butyl]-4-oxo-1-azetidinecarboxamide A solution of S-(R*,S*)]4-(((3,3-diethyl-1-((4-methylphenyl)butylamino)carbonyl)-4-oxo-2-azetidinyl) oxy)benzoyl chloride (3.8 mmol), prepared as in Example 11A, in 50 ml of methylene chloride was cooled in an ice bath and a solution of 0.70 gm of N-methylpiperazine in 10 ml of methylene chloride was added over 5 min. The reaction was stirred for 1 hr and was then poured into a mixture of ice water and 10% potassium carbonate. The product was extracted with two portions of methylene chloride and each methylene chloride layer was washed with a portion of brine. The methylene chloride layers were combined, dried over sodium sulfate and evaporated. The residue was purified with flash chromatography using ethyl acetate, then 2% triethylamine/10% methanol/88% ethyl acetate to afford 2.1 gm of the title compound as a white solid.

| Analysis: | $C_{30}H_{42}N_4O_4$ |
|---|---|
| Calc: | C, 69.64; H, 7.92; N, 10.48 |
| Found: | C, 69.62; H, 8.23; N, 10.46 |

EXAMPLE 20

[S-(R*,S*)]-2-[4-[[(4-Methyl)piperazin-1-yl] carbonyl]phenoxy]-((3,3-diethyl-N-[1-(3,4-methylenedioxyphenyl)butyl]-4-oxo-1-azetidinecarboxamide When [S-(R*,S*)]4-(((3,3-diethyl-1-((3,4-methylenedioxyphenyl)butylamino)carbonyl)-4-oxo-2-azetidinyl)oxy)benzoyl chloride (3.1 mmol), prepared as in Example 11A, was reacted with N-methylpiperazine as in Example 19, there was obtained 1.75 gm of the title compound.

| Analysis: | $C_{31}H_{40}N_4O_6$ |
|---|---|
| Calc: | C, 65.94; H, 7.14; N, 9.92 |
| Found: | C, 65.80; H, 7.31; N, 10.05 |

EXAMPLE 21

[S-(R*,S*)]2-[4-[[(4-Hydroxyethyl)piperazin-1-yl] carbonyl]phenoxy]-((3,3-diethyl-N-[1-(methylphenyl)butyl]-4-oxo-1-azetidinecarboxamide When [S-(R*,S*)]-4-(((3,3-diethyl-1-((4-methylphenyl) butylamino)carbonyl)-4-oxo-2-azetidinyl)oxy)benzoyl chloride (3.8 mmol), prepared as in Example 11A, was reacted with N-(2-hydroxyethyl)piperazine (7.6 mmol) and diisopropylethylamine (3.8 mmol) as in Example 19, there was obtained 2.1 gm of the title compound.

| Analysis: | $C_{32}H_{44}N_4O_5$ |
|---|---|
| Calc: | C, 68.06; H, 7.85; N, 9.92 |
| Found: | C, 67.88; H, 7.87; N, 10.17 |

EXAMPLE 22

[S-(R*,S*)]2-[4-[[(4-Hydroxyethyl)piperazin-1-yl] carbonyl]phenoxy]-((3,3-diethyl-N-[1-(3,4-methylenedioxyphenyl)butyl]-4-oxo-1-azetidinecarboxamide When [S-(R*,S*)]-4-(((3,3-diethyl-1-((3,4-methylenedioxyphenyl)butylamino)carbonyl)-4-oxo-2-azetidinyl)oxy)benzoyl chloride (3.1 mmol), prepared as in Example 11A, was reacted with N-(2-hydroxyethyl) piperazine (6.2 mmol) and diisopropylethylamine (3.1 mmol) as in Example 19, there was obtained 1.50 gm of the title compound.

| Analysis: | $C_{32}H_{42}N_4O_7$.1.5H2O |
|---|---|
| Calc: | C, 61.94; H, 6.89; N, 9.06 |
| Found: | C, 61.95; H, 6.92; N, 8.96 |

EXAMPLE 23

[S-(R*,S*)]-2-[4-[[(4-Cyclopropyl)piperazin-1-yl] carbonyl]phenoxy]-((3,3-diethyl-N-[1-(4-methylphenyl)butyl]-4-oxo-1-azetidinecarboxamide To a solution of [S-(R*,S*)]-4-(((3,3-diethyl-1-((4-methylphenyl)butylamino)carbonyl)-4-oxo-2-azetidinyl) oxy)benzoyl chloride (3.8 mmol), prepared as in Example 11A, in 50 ml of methylene chlorine was added N-(cyclopropyl)piperazine dihydrochloride (5.7 mmol) and then a solution of diisopropylethylamine (15.8 mmol) in 10 ml of methylene chloride was added over 5 min with ice-bath cooling. The reaction was stirred for 1 hr at 0° C. and then poured into ice water. The product was extracted with two portions of methylene chloride and each methylene chloride layer was washed with a portion of brine. The methylene chloride layers were combined, dried over sodium sulfate and ethyl acetate/50% hexanes, then 70% ethyl acetate/30% hexanes to afford 2.1 gm of the title compound as a white solid.

| Analysis: | $C_{32}H_{42}N_4O_4$ |
|---|---|
| Calc: | C, 70.69; H, 7.91; N, 9.99 |
| Found: | C, 70.62; H, 8.04; N, 9.95 |

EXAMPLE 24

[S-(R*,S*)]2-[4-[[(4-Cyclopropyl)piperazin-1-yl] carbonyl]phenoxy]-((3,3-diethyl-N-[1-(3,4-methylenedioxyphenyl)butyl]-4-oxo-1-azetidinecarboxamide When [S-(R*,S*)]4-(((3,3-diethyl-1-((3,4-methylenedioxyphenyl)butylamino)carbonyl)-4-oxo-2-azetidinyl)oxy)benzoyl chloride (3.1 mmol), prepared as in Example 11A, was reacted with N-(cyclopropyl)piperazine (4.6 mmol) and diisopropylethylamine (9.3 mmol) as in Example 23, there was obtained 1.80 gm of the title compound.

| Analysis: | $C_{32}H_{42}N_4O_7$ |
|---|---|
| Calc: | C, 67.10; H, 7.17; N, 9.49 |
| Found: | C, 67.03; H, 7.31; N, 9.47 |

EXAMPLE 25

[S-(R*,S*)]-2-[4-[[(4-Piperazin-1-yl)carbonyl] phenoxy]-((3,3-diethyl-N-[1-(4-methylphenyl)butyl] -4-oxo-1-azetidinecarboxamide Step A:

[S-R*,S*)]2-[4-[[(4-(t-Butoxycarbonyl))piperazin-1-yl] carbonyl]phenoxy]-((3,3-diethyl-N-[1-(4-methylphenyl) butyl]-4-oxo-1-azetidinecarboxamide

[S-(R*,S *)]4-(((3,3-Diethyl-1-((4-methylphenyl) butylamino)carbonyl)-4-oxo-2-azetidinyl)oxy))benzoyl chloride (0.4 mmol), prepared as in Example 11A, was reacted with N-(t-butoxycarbonyl)piperazine (0.6 mmol) and triethylamine (1.2 mmol) as in Example 23. The crude, title product so obtained was used directly in the following Step B.

Step B:

[S-R*,S*)]-2-[4-[(Piperazin-1-yl)carbonyl]phenoxy]-((3, 3-diethyl-N-[1-(4-methylphenyl)butyl-1-4-oxo-1-azetidinecarboxamide The product from Step A was dissolved in 0.5 ml of anisole and 2 ml of cold TFA was added. The reaction was stirred at 0° C. for 1 hr and was then diluted with methylene chloride and evaporated. The residue was taken up in methylene chloride, washed with 10% sodium carbonate and brine, dried over sodium sulfate and concentrated. The residue was purified by flash chromatography using 5, then 10% methanol/methylene chloride to afford 0.212 gm of title product.

| Analysis: | $C_{30}H_{40}N_4O_5$ .1H2O |
|---|---|
| Calc: | C, 66.89; H, 7.85; N, 10.40 |
| Found: | C, 67.06; H, 7.55; N, 10.30 |

EXAMPLE 26

[S-(R*,S*)]-2-[4-[[(4-Piperazin-1-yl)carbonyl] phenoxy]-((3,3-diethyl-N-[1-(3,4-methylenedioxyphenyl)butyl]-4-oxo-1-azetidinecarboxamide Step A:

[S-R*,S*)]-2-[4-[[(4-Benzyloxycarbonyl)Piperazin-1-yl] carbonyl]phenoxy]-((3,3-diethyl-N-[1-3,4-methylenedioxyphenyl)butyl]-4-oxo-1-azetidinecarboxamide When [S-(R*,S*)]-4-(((3,3-diethyl-1-((3,4-methylenedioxyphenyl)butylamino)carbonyl)-4-oxo-2-azetidinyl)oxy)benzoyl chloride (0.41 mmol), prepared as in Example 11A, was reacted with N-(benzyloxycarbonyl) piperazine (0.77 mmol) and diisopropylethylamine (1.6 mmol) as in Example 23, there was obtained 290 mg of the title compound.

Step B:

[S-R*,S*)]2-[4-[(Piperazin-1-yl)carbonyl]phenoxy]-((3, 3-diethyl-N-[1-(3,4-methylenedioxyphenyl)butyl-4-oxo-1-azetidinecarboxamide A solution of 250 mg of material from Example 26, Step A in 10 ml of ethanol was hydrogenated at 40 p.s.i. over 50 mg of 10% Pd/C for 16 hrs. The reaction was filtered and evaporated. The residue was purified by preparative TLC eluting with 2%

TEA/10% methanol/88% ethyl acetate to afford 150 mg of title product.

| Analysis: | $C_{30}H_{38}N_4O_6$.3H2O |
|---|---|
| Calc: | C, 59.59; H, 7.33; N, 9.29 |
| Found: | C, 59.66; H, 7.65; N, 9.61 |

What is claimed is:

1. A Method of treating an elastase mediated disease selected from the group consisting of emphysema, bronchial inflammation, chronic bronchitis, cystic fibrosis, and acute respiratory distress syndrome in a patient having said disease comprising the administration of a non-toxic therapeutically effective amount of a compound of Formula

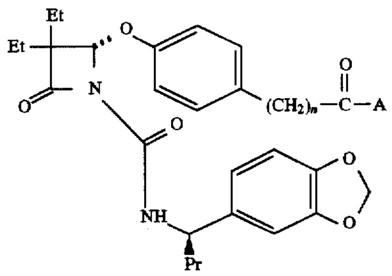

when n and A are:

n A 1 4-morpholinyl, 2 1—$N(CH_3)CH_2CH_2N(CH_3)_2$, 3 0—$N(CH_3)CH_2CH_2N(CH_3)_2$, 4 0—$N(Et)_2$, 5 0—$N(CH_3)$(n-Bu), 6 0 4-methyl-1-piperazinyl, 7 0—$N(CH_3)CH_2CH_2N(CH_3)CH_2Ph$, 8 0 4-cyclopropyl-1-piperazinyl, 9 0 1-piperazinyl, 10 0 4-(2-hydroxyethyl)-1-piperazinyl, or 11 0 4-morpholinyl.

2. A method according to claim 1 wherein the compound is [S-(R*,S*)]-2-[4-[[4-methylpiperazin-1-yl]carbonyl] phenoxy]-3,3-diethyl-N-[1-(3,4-methylenedioxyphenyl) butyl]-4-oxo-1-azetidine-carboxamide, or a pharmaceutically acceptable salt thereof.

3. A method of treating cystic fibrosis according to claim 2 wherein the compound is

[S-(R*,S*)]-2-[4-[[4-methylpiperazin-1-yl]carbonyl] phenoxy]-3,3-diethyl-N-[1-(3,4-methylenedioxyphenyl)butyl]-4-oxo-1-azetidinecarboxamide, or a pharmaceutically acceptable salt thereof.

4. A Method of treating an elastase mediated disease selected from the group consisting of emphysema, bronchial inflammation, chronic bronchitis, cystic fibrosis, and acute respiratory distress syndrome in a patient having said disease comprising the administration of a non-toxic therapeutically effective amount of a compound selected from (a) [S-(R*,S*)]-2-[4-[[[2-(dimethylamino)ethyl] methylamino]carbonyl]-phenoxy]-3,3-diethyl-N-[1-(4-methylphenyl)butyl]-4-oxo-1-azetidine-carboxamide, (b) [S-(R*,S*)]-2-[4-[[[2-(dimethylamino)ethyl] methylamino]carbonyl]-phenoxy]-3,3-diethyl-N-[1-(3,4-methylenedioxy-phenyl)butyl]-4-oxo-1-azetidine-carboxamide, (c) [S-(R*,S*)]-2-[4-[[4-methylpiperazin-1-yl]carbonyl] phenoxy]-3,3-diethyl-N-[1-(4-methylphenyl)butyl]-4-oxo-1-azetidinecarboxamide, (d) [S-(R*,S*)]-2-[4-[[4-methylpiperazin-1-yl]carbonyl] phenoxy]-3,3-diethyl-N-[1-(3,4-methylenedioxy-phenyl)butyl]-4-oxo-1-azetidine-carboxamide, (e) [S-(R*,S*)]-2-[4-[[4-cyclopropylpiperazin-1-yl]-carbonyl]phenoxy]-3,3-diethyl-N-[1-(4-methylphenyl) butyl]-4-oxo-1-azetidine-carboxamide, (f) [S-(R*,S*)]-2-[4-[[4-cyclopropylpiperazin-1-yl] carbonyl]phenoxy]-3,3-diethyl-N-[1-(3,4-methylenedioxyphenyl)butyl]-4-oxo-1-azetidine-carboxamide, (g) [S-(R*,S*)]-2-[4-[[piperazin-1-yl]carbonyl]phenoxy]-3,3-diethyl-N-[1-(4-methylphenyl)butyl]-4-oxo-1-azetidinecarboxamide, (h) [S-(R*,S*)]-2-[4-[[piperazin-1-yl]carbonyl]-phenoxy] -3,3-diethyl-N-[1-(3,4-methylenedioxyphenyl)butyl]-4-oxo-1-azetidinecarboxamide, (i) [S-(R*,S*)]-2-[4-[[((2-dimethylamino)ethyl) ethylamino]carbonyl]-phenoxy]-3,3-diethyl-N-[1-(4-methylphenyl)butyl]-4-oxo-1-azetidinecarboxamide, (j) [S-(R*,S*)]-2-[4-[[((2-diethylamino)ethyl) ethylamino]carbonyl]-phenoxy]-3,3-diethyl-N-[1-(4-methylphenyl)butyl]-4-oxo-1-azetidinecarboxamide, (k) [S-(R*,S*)]-2-[4-[[(4-(2-hydroxyethyl))piperazin-1-yl]carbonyl]-phenoxy]-3,3-diethyl-N-[1-(4-methylphenyl)butyl]-4-oxo-1-azetidinecarboxamide, (l) [S-(R*,S*)]-2-[4-[[(4-(2-hydroxyethyl))piperazin-1-yl]carbonyl]-phenoxy]-3,3-diethyl-N-[1-(3,4,-methylenedioxyphenyl)butyl]-4-oxo-1-azetidinecarboxamide, or (m) [S-(R*,S*)]-2-[4-[[(4-(ethoxycarbonylmethyl)) piperazin-1-yl]-carbonyl]phenoxy]-3,3-diethyl-N-[1-(3,4-methylenedioxyphenyl)-butyl]-4-oxo-1-azetidinecarboxamide.

5. A method of treating an elastase mediated disease selected from the group consisting of rheumatoid arthritis and osteoarthritis in a patient having said disease comprising the administration of a non-toxic therapeutically effective amount of a compound of Formula

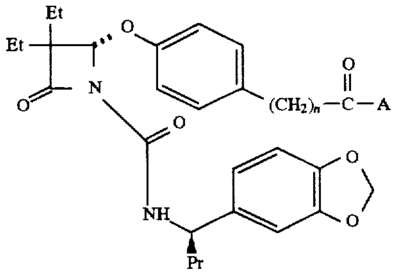

where n and A are:

| | n | A |
|---|---|---|
| 1 | 1 | 4-morpholinyl, |
| 2 | 1 | $-N(CH_3)CH_2CH_2N(CH_3)_2$, |
| 3 | 0 | $-N(CH_3)CH_2CH_2N(CH_3)_2$, |
| 4 | 0 | $-N(Et)_2$, |
| 5 | 0 | $-N(CH_3)$(n-Bu), |
| 6 | 0 | 4-methyl-1-piperazinyl, |
| 7 | 0 | $-N(CH_3)CH_2CH_2N(CH_3)CH_2Ph$, |
| 8 | 0 | 4-cyclopropyl-1-piperazinyl, |
| 9 | 0 | 1-piperazinyl, |
| 10 | 0 | 4-(2-hydroxyethyl)-1-piperazinyl, or |
| 11 | 0 | 4-morpholinyl. |

6. A method according to claim 5 wherein the compound is [S-(R*,S*)]-2-[4-[[4-methylpiperazin-1-yl]carbonyl] phenoxy]-3,3-diethyl-N-[1-(3;4-methylenedioxyphenyl) butyl]-4-oxo-1-azetidinecarboxamide, or a pharmaceutically acceptable salt thereof.

7. A method of treating a elastase mediated disease selected from the group consisting of rheumatoid arthritis and osteoarthritis in a patient having said disease comprising the administration of a non-toxic therapeutically effective amount of a compound selected from (a) [S-(R*,S*)]-2-[4-[[[2-(dimethylamino)ethyl] methylamino]carbonyl]-phenoxy]-3,3-diethyl-N-[1-(4-methylphenyl)butyl]-4-oxo-1-azetidinecarboxamide, (b) [S-(R*,S*)]-2-[4-[[[2-(dimethylamino)ethyl] methylamino]carbonyl]-phenoxy]-3,3-diethyl-N-[1-(3,4-methylenedioxy-phenyl)butyl]-4-oxo-1-azetidine-carboxamide, (c) [S-(R*,S*)]-2-[4-[[4-methylpiperazin-1-yl]carbonyl] phenoxy]-3,3-diethyl-N-[1-(4-methylphenyl)butyl]-4-oxo-1-azetidinecarboxamide, (d) [S-(R*,S*)]-2-[4-[[4-methylpiperazin-1-yl]carbonyl] phenoxy]-3,3-diethyl-N-[1-(3,4-methylenedioxy-phenyl)butyl]-4-oxo-1-azetidine-carboxamide, (e) [S-(R*,S*)]-2-[4-[[4-cyclopropylpiperazin-1-yl]-carbonyl]phenoxy]-3,3-diethyl-N-[1-(4-methylphenyl) butyl]-4-oxo-1-azetidine-carboxamide, (f) [S-(R*,S*)-2-[4-[[4-cyclopropylpiperazin-1-yl] carbonyl]phenoxy]-3,3-diethyl-N-[1-(3,4-methylenedioxyphenyl)butyl]-4-oxo-1-azetidinecarboxamide, (g) [S-(R*,S*)]-2-[4-[[piperazin-1-yl]carbonyl]phenoxy]-3,3-diethyl-N-[1-(4-methylphenyl)butyl]-4-oxo-1-azetidinecarboxamide, or (h) [S-(R*,S*)]-2-[4-[[piperazin-1-yl]carbonyl]-phenoxy] -3,3-diethyl-N-[1-(3,4-methylenedioxyphenyl)butyl]-4-oxo-1-azetidinecarboxamide, (i) [S-(R*,S*)]-2-[4-[[((2dimethylamino)ethyl) ethylamino]carbonyl]4-oxo-1-phenoxy]-3,3-diethyl-N-[1(4-methylphenyl)butyl]-

(j) [S-(R*,S*)]-2-[4-[[((2-diethylamino)ethyl) ethylamino]carbonyl]-phenoxyl]-3,3-diethyl-N-[1-(4-methylphenyl)butyl]-4-oxo-1-azetidinecarboxamide, (k) [S-(R*,S*)]-2-[4-[[(4-(2-hydroxyethyl))piperazin-1-yl]carbonyl]-phenoxy]-3,3-diethyl-N-[1-(4-methylphenyl)butyl]-4-oxo-1-azetidinecarboxamide, (l) [S-(R*,S*)]-2-[4-[[(4-(2-hydroxyethyl))piperazin-1-yl]carbonyl]-phenoxy]-3,3-diethyl-N-[1-(3,4,-methylenedioxyphenyl)butyl]-4-oxo-1-azetidinecarboxamide, or (m) [S-(R*,S*)]-2-[4-[[(4-(ethoxycarbonylmethyl)) piperazin-1-yl]-carbonyl]phenoxy]-3,3-diethyl-N-[1-(3,4-methylenedioxyphenyl)-butyl]-4-oxo-1-azetidinecarboxamide.

8. Method of treating a disease selected from the group consisting of glomerulonephritis, spondylitis, lupus, psoriasis, atherosclerosis, sepsis, septicemia, shock, myocardial infarction, reperfusion injury, and periodontitis in a patient in need of such treatment comprising the administration therapeutically effective amount of a compound of Formula

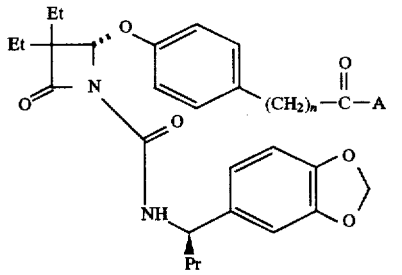

when n and A are:

| | n | A |
|---|---|---|
| 1 | 1 | 4-morpholinyl, |
| 2 | 1 | $—N(CH_3)CH_2CH_2N(CH_3)_2$, |
| 3 | 0 | $—N(CH_3)CH_2CH_2N(CH_3)_2$, |
| 4 | 0 | $—N(Et)_2$, |
| 5 | 0 | $—N(CH_3)$(n-Bu), |
| 6 | 0 | 4-methyl-1-piperazinyl, |
| 7 | 0 | $—N(CH_3)CH_2CH_2N(CH_3)CH_2Ph$, |
| 8 | 0 | 4-cyclopropyl-1-piperazinyl, |
| 9 | 0 | 1-piperazinyl, |
| 10 | 0 | 4-(2-hydroxyethyl)-1-piperazinyl, or |
| 11 | 0 | 4-morpholinyl. |

9. A method according to claim 8 wherein the compound is [S-(R*,S*)]-2-[4-[[4-methylpiperazin-1-yl]carbonyl] phenoxy]-3,3-diethyl-N-[1-(3,4-methylenedioxyphenyl) butyl]-4-oxo-1-azetidinecarboxamide, or a pharmaceutically acceptable salt thereof.

10. Method of treating a disease selected from the group consisting of glomerulonephritis, spondylitis, lupus, psoriasis, atherosclerosis, sepsis, septicemia, shock, myocardial infarction, reperfusion injury, and periodontitis in a patient in need of such treatment comprising the administration therapeutically effective amount of a compound selected from (a) [S-(R*,S*)]-2-[4-[[[2-(dimethylamino)ethyl] methylamino]carbonyl]-phenoxy]-3,3-diethyl-N-[1-(4-methylphenyl)butyl]-4-oxo-1-azetidinecarboxamide, (b) [S-(R*,S*)]-2-[4-[[[2-(dimethylamino)ethyl] methylamino]carbonyl]-phenoxy]-3,3-diethyl-N-[1-(3,4-methylenedioxy-phenyl)butyl]-4-oxo-1-azetidinecarboxamide, (c) [S-(R*,S*)]-2-[4-[[4-methylpiperazin-1-yl]carbonyl] phenoxy]-3,3-diethyl-N-[1-(4-methylphenyl)butyl]-4-oxo-1-azetidinecarboxamide, (d) [S-(R*,S*)]-2-[4-[[4-methylpiperazin-1-yl]carbonyl] phenoxy]-3,3-diethyl-N-[1-(3,4-methylenedioxyphenyl)butyl]-4-oxo-1-azetidine-carboxamide, (e) [S-(R*,S*)]-2-[4-[[4-cyclopropylpiperazin-1-yl]-carbonyl]phenoxy]-3,3-diethyl-N-[1-(4-methylphenyl) butyl]-4-oxo-1-azetidine-carboxamide, (f) [S-(R*,S*)]-2-[4-[[4-cyclopropylpiperazin-1-yl] carbonyl]phenoxy]-3,3-diethyl-N-[1-(3,4-methylenedioxyphenyl)butyl]-4-oxo-1-azetidinecarboxamide, (g) [S-(R*,S*)]-2-[4-[[piperazin-1-yl]carbonyl]phenoxy]-3,3-diethyl-N-[1-(4-methylphenyl)butyl]-4-oxo-1-azetidinecarboxamide, or (h) [S-(R*,S*)]-2-[4-[[piperazin-1-yl]carbonyl]-phenoxy] -3,3-diethyl-N-[1-(3,4-methylenedioxyphenyl)butyl]-4-oxo-1-azetidinecarboxamide, (i) [S-(R*,S*)]-2-[4-[[((2-dimethylamino)ethyl) ethylamino]carbonyl]-phenoxy]-3,3-diethyl-N-[1-(4-methylphenyl)butyl]-4-oxo-1-azetidinecarboxamide, (j) [S-(R*,S*)]-2-[4-[[((2-diethylamino)ethyl) ethylamino]carbonyl]-phenoxy]-3,3-diethyl-N-[1-(4-methylphenyl)butyl]-4-oxo-1-azetidinecarboxamide, (k) [S-(R*,S*)]-2-[4-[[(4-(2-hydroxyethyl))piperazin-1-yl]carbonyl]-phenoxy]-3,3-diethyl-N-[1-(4-methylphenyl)butyl]-4-oxo-1-azetidinecarboxamide, (l) [S-(R*,S*)]-2-[4-[[(4-(2-hydroxyethyl))piperazin-1-yl]carbonyl]-phenoxy]-3,3-diethyl-N-[1-(3,4,-methylenedioxyphenyl)butyl]-4-oxo-1-azetidinecarboxamide, or (m) [S-(R*,S*)]-2-[4-[[(4-(ethoxycarbonylmethyl)) piperazin-1-yl]-carbonyl]phenoxy]-3,3-diethyl-N-[1-(3,4-methylenedioxyphenyl)-butyl]-4-oxo-1-azetidinecarboxamide.

* * * * *

UNITED STATES PATENT AND TRADEMARK OFFICE

CERTIFICATE OF CORRECTION

PATENT NO. : 5,747,485

DATED : 5/5/98

INVENTOR(S) : James B. Doherty, et al.

It is certified that error appears in the above-indentified patent and that said Letters Patent is hereby corrected as shown below:

Column 60, lines 65-67, should be deleted and substitute therefore the following:

--(i)[S-(R*,S*)]-2-[4-[[((2-dimethylamino)ethyl)ethylamino]carbonyl]-phenoxy]-3,3-diethyl-N-[1-(4-methylphenyl) butyl]-4-oxo-1-azetidinecarboxamide, Signed and Sealed this Eighteenth Day of August, 1998

Attest:

Bruce Lehman

BRUCE LEHMAN

Attesting Officer

*Commissioner of Patents and Trademarks*

UNITED STATES PATENT AND TRADEMARK OFFICE
CERTIFICATE OF CORRECTION

PATENT NO. : 5,747,485
DATED : May 5, 1998
INVENTOR(S) : James Doherty, et al

It is certified that error appears in the above-identified patent and that said Letters Patent is hereby corrected as shown below:

On the title page, item [54] should read:

-- Substituted Azetidinones As Anti-inflammatory and AntiDegenerative Agents --.

Signed and Sealed this

Second Day of February, 1999

Attest:

*Acting Commissioner of Patents and Trademarks*

*Attesting Officer*